United States Patent
Goodman et al.

(10) Patent No.: US 11,452,748 B2
(45) Date of Patent: *Sep. 27, 2022

(54) PROBIOTIC FORMULATIONS AND METHODS FOR USE

(71) Applicants: Research Institute at Nationwide Children's Hospital, Columbus, OH (US); Ohio State Innovation Foundation, Columbus, OH (US)

(72) Inventors: Steven D. Goodman, Hilliard, OH (US); Lauren O. Bakaletz, Hilliard, OH (US); Gail Besner, Columbus, OH (US); Michael Bailey, Columbus, OH (US)

(73) Assignees: Research Institute at Nation Children's Hospital, Columbus, OH (US); Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/449,320

(22) Filed: Jun. 21, 2019

(65) Prior Publication Data

US 2020/0155620 A1     May 21, 2020

Related U.S. Application Data

(63) Continuation of application No. 15/257,673, filed on Sep. 6, 2016, now Pat. No. 10,369,176, which is a continuation of application No. PCT/US2015/019059, filed on Mar. 5, 2015.

(60) Provisional application No. 61/949,058, filed on Mar. 6, 2014.

(51) Int. Cl.
    *A61K 35/747*      (2015.01)
    *A61K 9/16*      (2006.01)
    *A23L 33/135*      (2016.01)
    *A23L 33/195*      (2016.01)

(52) U.S. Cl.
    CPC .......... *A61K 35/747* (2013.01); *A23L 33/135* (2016.08); *A23L 33/195* (2016.08); *A61K 9/1611* (2013.01); *A61K 9/1647* (2013.01); *A61K 9/1652* (2013.01); *A61K 9/1658* (2013.01); *A23V 2002/00* (2013.01); *A23V 2200/3202* (2013.01); *A23V 2200/3204* (2013.01)

(58) Field of Classification Search
None
See application file for complete search history.

(56) References Cited

U.S. PATENT DOCUMENTS

| | | | |
|---|---|---|---|
| 5,549,908 A | 8/1996 | Smith et al. | |
| 6,486,314 B1 | 11/2002 | Van Geel-Schutten et al. | |
| 6,551,795 B1 | 4/2003 | Rubenfield et al. | |
| 7,241,867 B2 | 7/2007 | Bakaletz et al. | |
| 7,435,595 B2 | 10/2008 | Boehm et al. | |
| 7,638,282 B2 | 12/2009 | Bakaletz et al. | |
| 7,816,086 B2 | 10/2010 | Bakaletz et al. | |
| 7,981,676 B2 | 7/2011 | Boehm et al. | |
| 7,998,490 B2 | 8/2011 | Bakaletz et al. | |
| 8,236,494 B2 | 8/2012 | Bakaletz et al. | |
| 8,283,114 B2 | 10/2012 | Bakaletz et al. | |
| 8,628,917 B2 | 1/2014 | Bakaletz et al. | |
| 8,652,773 B2 | 2/2014 | Bakaletz et al. | |
| 8,758,764 B2 | 6/2014 | Masignani et al. | |
| 8,999,291 B2 | 4/2015 | Goodman et al. | |
| 9,005,682 B2 | 4/2015 | Sprenger et al. | |
| 9,034,642 B2 | 5/2015 | Bakaletz et al. | |
| 9,278,069 B2 | 3/2016 | Berkland et al. | |
| 9,504,739 B2 | 11/2016 | Berkes et al. | |
| 9,554,590 B2 | 1/2017 | Quintens et al. | |
| 9,603,878 B2 | 3/2017 | Berry et al. | |
| 9,610,307 B2 | 4/2017 | Berry et al. | |
| 9,622,956 B2 | 4/2017 | Schaeffer-Korbylo et al. | |
| 9,687,449 B2 | 6/2017 | Harel | |
| 9,713,631 B2 | 7/2017 | Berkes et al. | |
| 9,717,765 B2 | 8/2017 | Berkes et al. | |
| 10,369,176 B2* | 8/2019 | Goodman | ................. A61P 1/00 |
| 10,624,934 B2* | 4/2020 | Goodman | ............ A61K 9/1652 |
| 2005/0059633 A1* | 3/2005 | Van Geel-Schuten | ...................... C12P 19/08 514/54 |
| 2005/0112235 A1 | 5/2005 | Shefer et al. | |
| 2005/0170504 A1 | 8/2005 | Boehm et al. | |
| 2005/0221439 A1 | 10/2005 | Bakaletz et al. | |
| 2005/0266069 A1 | 12/2005 | Simmons et al. | |
| 2007/0207210 A1 | 9/2007 | Brown et al. | |

(Continued)

FOREIGN PATENT DOCUMENTS

DE    20 2013 103 204 U1    7/2013
EP        3 113 630 A2    1/2017

(Continued)

OTHER PUBLICATIONS

Olson et al, Am. J. Physiol. Gastrointest. Liver Physiol., 2018, 315:G408-G419, first published: May 31, 2018 (Year: 2018).*

(Continued)

*Primary Examiner* — Nita M. Minnifield
(74) *Attorney, Agent, or Firm* — Foley & Lardner LLP

(57) ABSTRACT

Provided herein are compositions comprising a biocompatible microsphere, a biofilm-generating probiotic bacterium, a prebiotic, and/or a prebiofilmic. Methods for preparing and formulating the compositions and methods for treating or preventing a disease using the compositions are also provided.

12 Claims, 4 Drawing Sheets

Specification includes a Sequence Listing.

(56) References Cited

U.S. PATENT DOCUMENTS

| | | |
|---|---|---|
| 2007/0264256 A1 | 11/2007 | Bakaletz et al. |
| 2007/0286822 A1 | 12/2007 | Sanders et al. |
| 2009/0155912 A1 | 6/2009 | Boehm et al. |
| 2010/0166771 A1 | 7/2010 | Bakaletz et al. |
| 2010/0303723 A1 | 12/2010 | Farokhzad et al. |
| 2010/0310569 A1 | 12/2010 | Bakaletz et al. |
| 2011/0008493 A1* | 1/2011 | Zorea ............... A21D 8/045 426/61 |
| 2011/0027328 A1 | 2/2011 | Baig et al. |
| 2011/0135646 A1 | 6/2011 | Bakaletz et al. |
| 2011/0236306 A1 | 9/2011 | Goodman et al. |
| 2011/0293624 A1 | 12/2011 | Bakaletz et al. |
| 2012/0128701 A1 | 5/2012 | Goodman et al. |
| 2012/0189558 A1 | 7/2012 | Prendergast |
| 2012/0247993 A1* | 10/2012 | Palazzi ............ A61K 35/747 206/363 |
| 2013/0017204 A1 | 1/2013 | Bakaletz et al. |
| 2013/0078254 A1 | 3/2013 | Bakaletz et al. |
| 2014/0005649 A1 | 1/2014 | Burnett et al. |
| 2014/0010918 A1 | 1/2014 | Quintens et al. |
| 2014/0120107 A1 | 5/2014 | Bakaletz et al. |
| 2014/0127221 A1 | 5/2014 | Bakaletz et al. |
| 2014/0170126 A1 | 6/2014 | Duncker et al. |
| 2014/0356389 A1 | 12/2014 | Masignani et al. |
| 2014/0363410 A1 | 12/2014 | Bergonzelli Degonda et al. |
| 2014/0377192 A1 | 12/2014 | Schaeffer-Korbylo et al. |
| 2015/0010654 A1 | 1/2015 | Arnold et al. |
| 2015/0086542 A1 | 3/2015 | Goodman et al. |
| 2015/0086561 A1 | 3/2015 | Kauvar et al. |
| 2015/0110838 A1 | 4/2015 | Agrawal |
| 2015/0166641 A1 | 6/2015 | Goodman et al. |
| 2015/0173374 A1 | 6/2015 | Majeed et al. |
| 2015/0197558 A1 | 7/2015 | Kauvar et al. |
| 2015/0218231 A1 | 8/2015 | Bakaletz et al. |
| 2015/0247993 A1 | 9/2015 | Ishizaka |
| 2015/0290140 A1 | 10/2015 | Singh et al. |
| 2016/0089363 A1 | 3/2016 | Borody |
| 2016/0095316 A1 | 4/2016 | Goodman et al. |
| 2016/0120915 A1 | 5/2016 | Blaser et al. |
| 2016/0143961 A1 | 5/2016 | Berry et al. |
| 2016/0175440 A1 | 6/2016 | Goodman et al. |
| 2016/0193258 A1 | 7/2016 | Berry et al. |
| 2016/0194384 A1 | 7/2016 | Goodman et al. |
| 2016/0199424 A1 | 7/2016 | Berry et al. |
| 2016/0223553 A1 | 8/2016 | Sears et al. |
| 2016/0228476 A1 | 8/2016 | Cutcliffe et al. |
| 2016/0235792 A1 | 8/2016 | Berry et al. |
| 2016/0237145 A1 | 8/2016 | Kauvar et al. |
| 2016/0244489 A1 | 8/2016 | Masignani et al. |
| 2016/0271188 A1 | 9/2016 | Berry et al. |
| 2016/0289278 A1 | 10/2016 | Bakaletz et al. |
| 2017/0056454 A1 | 3/2017 | Berkes et al. |
| 2017/0056455 A1 | 3/2017 | Berkes et al. |
| 2017/0128502 A1 | 5/2017 | Berkes et al. |
| 2017/0196914 A1 | 7/2017 | Mckenzie et al. |
| 2017/0196915 A1 | 7/2017 | Czarnecki-Maulden et al. |
| 2017/0206504 A1 | 7/2017 | Taylor et al. |
| 2017/0209504 A1* | 7/2017 | Goodman ............ A61P 25/00 |
| 2017/0216377 A1 | 8/2017 | Berkes et al. |
| 2017/0281699 A1 | 10/2017 | Berkes et al. |
| 2017/0296600 A1 | 10/2017 | Rangavajla |
| 2017/0312321 A1 | 11/2017 | Rubio Nistal et al. |
| 2018/0000878 A1* | 1/2018 | Goodman ............ A61K 47/22 |
| 2018/0071344 A1 | 3/2018 | Berry et al. |
| 2018/0221422 A1 | 8/2018 | Keshtmand et al. |
| 2020/0155620 A1* | 5/2020 | Goodman ............ A61K 9/1658 |
| 2021/0100854 A1 | 4/2021 | Goodman et al. |
| 2021/0290701 A1 | 9/2021 | Besner et al. |

FOREIGN PATENT DOCUMENTS

| | | |
|---|---|---|
| JP | 2005-528324 A | 9/2005 |
| JP | 2006-512059 A | 4/2006 |
| JP | 2010-195786 A | 9/2010 |
| JP | 2010-535731 A | 11/2010 |
| JP | 2011-102250 A | 5/2011 |
| JP | 2011-201840 A | 10/2011 |
| JP | 2012-527898 A | 11/2012 |
| JP | 2013-510560 A | 3/2013 |
| JP | 2013-529893 | 7/2013 |
| JP | 2017-508754 A | 3/2017 |
| WO | WO-98/50018 A1 | 11/1998 |
| WO | WO-02/077183 A2 | 10/2002 |
| WO | WO-03/083045 A2 | 10/2003 |
| WO | WO-2010/138522 A2 | 12/2010 |
| WO | WO-2011/000123 A1 | 1/2011 |
| WO | WO-2013/007742 A1 | 1/2013 |
| WO | WO-2013/088045 A1 | 6/2013 |
| WO | WO-2014/067976 A1 | 5/2014 |
| WO | WO-2014/121304 A1 | 8/2014 |
| WO | WO-2015/134808 A2 | 9/2015 |
| WO | WO-2015134808 A2 * | 9/2015 ............ A61P 25/00 |
| WO | WO-2016/066763 A1 | 5/2016 |
| WO | WO-2020/028871 A1 | 2/2020 |

OTHER PUBLICATIONS

U.S. Appl. No. 15/649,352, filed Jul. 13, 2017, Goodman et al.

2nd Examination Report issued in Australian Application No. 2015227075 dated Mar. 6, 2019.

A. -L Cornaz Gudet et al., "Simple method of in vitro diffusion of nicotine across procine palatine mucosa", European Journal of Pharmaceutics and Biopharmaceutics, vol. 43, No. 3, Jun. 1, 1997, pp. 259-264.

Allaker, R.P. et al. (2015) "Non-conventional therapeutics for oral infections," Virulence 6(3):196-207.

Beer, S.J. et al. (1998) "Poly (lactic-glycolic) acid copolymer encapsulation of recombinant adenovirus reduces immunogenicity in vivo," Gene Therapy 5:740-746.

Ben, X-M. et al. (2008) "Low level of galacto-oligosaccharide in infant formula stimulates growth of intestinal Bifidobacteria and Lactobacilli," World J Gastroenterol. 14(42):6564-6568.

Boyle et al, Clinical and Experimental Allergy, 2009, 39:1117-1127 (Year: 2009).

Braegger et al, JPGN, Feb. 2011, 52/2:239-250. (Year: 2011).

Burdet et al., "Antibiotic-Induced Dysbiosis Predicts Mortality in an Animal Model of Clostridium difficile Infection", Antimicrobial Agents and Chemotherapy, vol. 62, No. 10, Sep. 24, 2018, Epub Jul. 30, 2018, pp. 1-12.

Catia Ornelas-Megiatto et al., "Aerosolized Antimicrobial Agents Based on Degradable Dextran Nanoparticles Loaded with Silver Carbene Complexes", Molecular Pharmaceutics, vol. 9, No. 11, Oct. 19, 20102, pp. 3012-3022.

Chavarri, M. et al. (2010) "Microencapsulation of a probiotic and prebiotic in alginate-chitosan capsules improves survival in simulated gastro-intestinal conditions," International Journal of Food Microbiology 142:185-189.

Chen et al, World J. Microbial. Biotechnol., 2012, 28/6:2447-2452. published online: Mar. 30, 2012 (Year: 2012).

Chen, C-C. et al. (2013) "Probiotics and the mechanisms of necrotizing enterocolitis," Seminars in Pediatric Surgery 22:94-100.

Cook, M.T. et al. (2012) "Microencapsulation of probiotics for gastrointestinal delivery," Journal of Controlled Release 162:56-67.

Cook, M.T. et al. (2014) "Microencapsulation of a symbiotic into PLGA/alginate multiparticulate gels," International Journal of Pharmaceutics 466:400-408.

Crittenden et al., "Synbiotic Microcapsules That Enhance Microbial Viability during Nonrefrigerated Storage and Gastrointestinal Transit", Applied and Environmental Microbiology, vol. 72, No. 3, Mar. 2006, pp. 2280-2282.

Examination Report No. 3 for Australian Application No. 2015227075 dated Mar. 13, 2019, 6 pages.

Extended European Search Report issued in EP 16825137.9 dated Feb. 14, 2019, 9 pages.

Final Office Action on U.S. Appl. No. 15/649,352 dated Apr. 5, 2019.

Final Office Action on U.S. Appl. No. 15/744,725 dated Dec. 17, 2018.

(56) References Cited

OTHER PUBLICATIONS

Foreign Action other than Search Report on JP 2018-38713 dated Aug. 8, 2019.
Foreign Search Report on EP 19154908.8 dated Sep. 18, 2019.
Francavilla et al, JPGN, Jul. 2016, vol. 63/Supplement 1, S36-S37 (Year: 2016).
Goodman, S.D. et al. (2011) "Biofilms can be dispersed by focusing the immune system on a common family of bacterial nucleoid-associated proteins," Mucosal Immunology 4(6):625-637.
Gustave, J.E. et al. (2013) "Targeting bacterial integration host factor to disrupt biofilms associated with cystic fibrosis," Journal of Cystic Fibrosis 12(4):384-389.
International Search Report and Written Opinion (ISA/EP) for International Application No. PCT/US2015/019059, dated Nov. 20, 2015.
International Search Report and Written Opinion (ISA/US) for International Application No. PCT/US2018/024604, dated Aug. 29, 2018.
International Search Report and Written Opinion (ISA/US) for PCT Patent Application No. PCT/US2016/042153, dated Sep. 27, 2016.
International Search Report and Written Opinion for PCT Application No. PCT/US2019/057279 dated Jan. 15, 2020, 17 pages.
Jaleh Varshosaz, "The promise of chitosan microspheres in drug delivery systems", Expert Opinion on Drug Delivery, vol. 4, No. 3, May 9, 2007. pp. 263-273.
Justice, S.S. et al. (2012) "Aberrant Community Architecture and Attenuated Persistence of Uropathogenic *Escherichia coli* in the Absence of Individual IHF Subunits," PLoS ONE 7(10):e48349, 1-11.
Kadajji, V.G. et al. (2011) "Water Soluble Polymers for Pharmaceutical Applications," Polymers 3:1972-2009.
Kumari, A. et al. (2010) "Biodegradable polymeric nanoparticles based drug delivery systems," Colloids and Surfaces B: Biointerfaces 75:1-18.
Lewis et al, British Journal of Nutrition, 2013, 110:1243-1252. first published online: Mar. 11, 2013 (Year: 2013).
Liao et al, Animal Nutrition. 2017, 3:331-343. available online: Jul. 8, 2017 (Year: 2017).
Mackos, A.R. et al. (2013) "Probiotic Lactobacillus Reuteri Attenuates the Stressor-Enhanced Severity of Citrobacter Rodentium Infection," Infect Immun. 81: 3253-3263.
Martin, C.R. et al. (2008) "Probiotics: Role in Pathophysiology and Prevention in Necrotizing Enterocolitis," Semin. Perinatol. 32:127-137.
Mashburn-Warren et al, Mol. Oral Microbial., 2017, 32:475-489 (Year: 2017).
Navarro, J.B. et al. (2017) "Enhanced Probiotic Potential of Lactobacillus reuteri When Delivered as a Biofilm on Dextranomer Microspheres That Contain Beneficial Cargo," Frontiers in Microbiology 8(489):15 pages.
Non-Final Office Action in U.S. Appl. No. 15/257,673, dated Dec. 22, 2017.
Non-Final Office Action issued in U.S. Appl. No. 15/744,725 dated May 17, 2018 (19 pages).
Non-Final Office Action dated Oct. 15, 2018 in co-pending U.S. Appl. No. 15/649,352 (21 pgs.).
Notice of Allowance dated Dec. 26, 2018 in co-pending U.S. Appl. No. 15/257,673 (6 pgs.).
Notice of Allowance on U.S. Appl. No. 15/257,673 dated Mar. 22, 2019.
Notice of Allowance on U.S. Appl. No. 15/649,352 dated Dec. 23, 2019.
Nowakowski, "Antimicrobial activity of nicotine against a spectrum of bacterial and fungal pathogens", J. Med. Microbiol., vol. 49., Dec. 31, 2000, pp. 674-675.
Office Action dated Oct. 18, 2018 in related Japanese Appl. 2016-555766 with English-language translation (20 pgs.).
Office Action dated Sep. 5, 2018 in co-pending U.S. Appl. No. 15/257,673.
Official Action issued in JP Patent No. 2016-555766 dated Apr. 2, 2019, 5 pages.
Olson et al, Am. J. Physiol. Gastrointest. Liver Physiol., 2018, 315:G408-G418. First published May 31, 2018 (Year: 2018).
Olson, J.K et al. (2016) "Harvesting the benefits of biofilms: A novel probiotic delivery system for the prevention of necrotizing enterocolitis," Journal of Pediatric Surgery 51:936-941.
Partial European Search Report issued in European Application No. 19154908.8 dated May 31, 2019, 12 pages.
Petreska Ivanovska, T. et al. (2014) "Comparative evaluation of viability of encapsulated Lactobacillus casei using two different methods of microencapsulation," International Journal of Pharmaceutical and Phytopharmacological Research 4(1):20-24 (Abstract only).
Pliszczak, D. et al. (2011) "Improvement of an encapsulation process for the preparation of pro- and prebiotics-loaded bioadhesive microparticles by using experimental design," European Journal of Pharmaceutical Sciences 44:83-92.
Reid et al, Beneficial Microbes, 2017, 8/4:521-533. (Year: 2017).
Rezaee et al, Current Nutrition and Food Science, 2014, 10:88-93. (Year: 2014).
Rocco et al: "Targeting the HUB protein prevents porphyromonas gingivalis from entering into preexisting biofilms" Journal of Bacteriology, 2018, vol. 200 (11), e00790-17, pp. 1-11.
Roselli, M. et al. (2017) "Immunomodulating effects of probiotics for microbiota modulation, gut heath and disease resistance in pigs," Food and Nutrition Research Center, Council for Agricultural Research and Economics, Rome, 00178, Italy, Animal Feed Science and Technology, Ahead of Print: (Abstract only).
Salas-Jara et al: "Biofilm forming Lactobacillus: New challenges for the development of Probiotics". Microorganisms, 2016, vol. 4, pp. 1-14.
Salmeron, Letters in Applied Microbiology, 2017, 65:114-124 (Year: 2017).
Sarmiento-Rubiano, L.A. et al. (2007) "Dietary supplementation with sorbitol results in selective enrichment of lactobacilli in rat intestine," Research in Microbiology 158:694-701.
Sathyabama, S. et al. (2014) "Co-encapsulation of probiotics with prebiotics on alginate matrix and its effect on viability in simulated gastric environment," LWT—Food Science and Technology 57:419-425.
Sultana, K. et al. (2000) "Encapsulation of probiotic bacteria with alginate-starch and evaluation of survival in simulated gastrointestinal conditions and in yoghurt," International Journal of Food Microbiology 62:47-55.
Thurnheer, T. et al. (2014) "Colonisation of gingival epithelia by subgingival biofilms in vitro: role of 'red complex' bacteria," Arch Oral Biol. 59(9):977-986.
UniProtKB: TrEMBL A0A0E4BIL9. Putative DNA-binding protein HU (2015) from www.uniprot.org/uniprot/A0A0E4BIL9.txt?version=3.
U.S. Office Action on U.S. Appl. No. 15/744,725 dated May 17, 2018.
Woischnig, A.K. et al. "High Affinity Native Human Monoclonal Antibody with Broad Cross-Species Biofilm Disrupting Activity" poster presented at IAAC Meeting on Sep. 20, 2015, available at www.trellisbio.com/assets/docs/ICAAC%20Biofilm%20Poster%2020150920.pdf.
Wu, H. et al. (2004) "Preparation of sodium fluoride-loaded gelatin microspheres, characterization and cariostatic studies," J Microencapsul. 21(8):889-903, Abstract.
Final Office Action on U.S. Appl. No. 16/437,921 dated Oct. 19, 2020.
Non-Final Office Action on U.S. Appl. No. 16/437,921 dated Mar. 12, 2020, 12 pages.
Smith et al., "Cystic Fibrosis Airway Epithelia Fail to Kill Bacteria Because of Abnormal Airway Surface Fluid," Cell, vol. 85, Apr. 19, 1996, pp. 229-236.
Wu et al. Development of dextran nanoparticles for stabilizing delicate proteins. Nanoscale Res Lett. Apr. 27, 2013;8(1):197.
Desiderio et al. "Intraphagocytic Killing of *Salmonella typhimurium* by Liposome-Encapsulated Cephalothin", The Journal of Infectious Diseases, vol. 148, No. 3, pp. 563-570) (1983).

(56) References Cited

OTHER PUBLICATIONS

U.S. Non-Final Office Action dated Feb. 3, 2022, from U.S. Appl. No. 16/437,921.
U.S. Non-Final Office Action dated Dec. 27, 2021, from U.S. Appl. No. 16/820,463.
U.S. Final Office Action dated Jun. 15, 2022, from U.S. Appl. No. 16/820,463.
U.S. Notice of Allowance dated Jun. 30, 2022, from U.S. Appl. No. 16/820,463.

* cited by examiner

SEQUENCE LISTING

```
<160> NUMBER OF SEQ ID NOS: 33

<210> SEQ ID NO 1
<211> LENGTH: 96
<212> TYPE: PRT
<213> ORGANISM: Haemophilus influenzae

<400> SEQUENCE: 1

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
            20                  25                  30

Glu Glu Ile Arg Leu Ser Leu Glu Ser Gly Gln Asp Val Lys Leu Ser
        35                  40                  45

Gly Phe Gly Asn Phe Glu Leu Arg Asp Lys Ser Ser Arg Pro Gly Arg
    50                  55                  60

Asn Pro Lys Thr Gly Asp Val Val Pro Val Ser Ala Arg Arg Val Val
65                  70                  75                  80

Thr Phe Lys Pro Gly Gln Lys Leu Arg Ala Arg Val Glu Lys Thr Lys
                85                  90                  95

<210> SEQ ID NO 2
<211> LENGTH: 136
<212> TYPE: PRT
<213> ORGANISM: Haemophilus influenzae

<400> SEQUENCE: 2

Met Arg Phe Val Thr Ile Phe Ile Asn His Ala Phe Asn Ser Ser Gln
1               5                   10                  15

Val Arg Leu Ser Phe Ala Gln Phe Leu Arg Gln Ile Arg Lys Asp Thr
            20                  25                  30

Phe Lys Glu Ser Asn Phe Leu Phe Asn Arg Arg Tyr Lys Phe Met Asn
        35                  40                  45

Lys Thr Asp Leu Ile Asp Ala Ile Ala Asn Ala Ala Glu Leu Asn Lys
    50                  55                  60

Lys Gln Ala Lys Ala Ala Leu Glu Ala Thr Leu Asp Ala Ile Thr Ala
65                  70                  75                  80

Ser Leu Lys Glu Gly Glu Pro Val Gln Leu Ile Gly Phe Gly Thr Phe
                85                  90                  95

Lys Val Asn Glu Arg Ala Ala Arg Thr Gly Arg Asn Pro Gln Thr Gly
                100                 105                 110
```

Ala Glu Ile Gln Ile Ala Ala Ser Lys Val Pro Ala Phe Val Ser Gly
        115                 120                 125

Lys Ala Leu Lys Asp Ala Ile Lys
        130                 135

<210> SEQ ID NO 3
<211> LENGTH: 96
<212> TYPE: PRT
<213> ORGANISM: Haemophilus influenzae

<400> SEQUENCE: 3

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
            20                  25                  30

Glu Glu Ile Arg Leu Ser Leu Glu Ser Gly Gln Asp Val Lys Leu Ser
        35                  40                  45

Gly Phe Gly Asn Phe Glu Leu Arg Asp Lys Ser Ser Arg Pro Gly Arg
    50                  55                  60

Asn Pro Lys Thr Gly Asp Val Val Pro Val Ser Ala Arg Arg Val Val
65                  70                  75                  80

Thr Phe Lys Pro Gly Gln Lys Leu Arg Ala Arg Val Glu Lys Thr Lys
                85                  90                  95

<210> SEQ ID NO 4
<211> LENGTH: 96
<212> TYPE: PRT
<213> ORGANISM: Haemophilus influenzae

<400> SEQUENCE: 4

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
            20                  25                  30

Glu Glu Ile Arg Leu Ser Leu Glu Ser Gly Gln Asp Val Lys Leu Ser
        35                  40                  45

Gly Phe Gly Asn Phe Glu Leu Arg Asp Lys Ser Ser Arg Pro Gly Arg
    50                  55                  60

Asn Pro Lys Thr Gly Asp Val Val Pro Val Ser Ala Arg Arg Val Val
65                  70                  75                  80

Thr Phe Lys Pro Gly Gln Lys Leu Arg Ala Arg Val Glu Lys Thr Lys
                85                  90                  95

<210> SEQ ID NO 5
<211> LENGTH: 99
<212> TYPE: PRT
<213> ORGANISM: Escherichia coli

<400> SEQUENCE: 5

Met Ala Leu Thr Lys Ala Glu Met Ser Glu Tyr Leu Phe Asp Lys Leu
1               5                   10                  15

Gly Leu Ser Lys Arg Asp Ala Lys Glu Leu Val Glu Leu Phe Phe Glu
            20                  25                  30

Glu Ile Arg Arg Ala Leu Glu Asn Gly Glu Gln Val Lys Leu Ser Gly
        35                  40                  45

Phe Gly Asn Phe Asp Leu Arg Asp Lys Asn Gln Arg Pro Gly Arg Asn
    50                  55                  60

```
Pro Lys Thr Gly Glu Asp Ile Pro Ile Thr Ala Arg Arg Val Val Thr
 65                  70                  75                  80

Phe Arg Pro Gly Gln Lys Leu Lys Ser Arg Val Glu Asn Ala Ser Pro
                 85                  90                  95

Lys Asp Glu

<210> SEQ ID NO 6
<211> LENGTH: 100
<212> TYPE: PRT
<213> ORGANISM: Pseudomonas aeruginosa

<400> SEQUENCE: 6

Met Gly Ala Leu Thr Lys Ala Glu Ile Ala Glu Arg Leu Tyr Glu Glu
  1               5                  10                  15

Leu Gly Leu Asn Lys Arg Glu Ala Lys Glu Leu Val Glu Leu Phe Phe
                 20                  25                  30

Glu Glu Ile Arg Gln Ala Leu Glu His Asn Glu Gln Val Lys Leu Ser
             35                  40                  45

Gly Phe Gly Asn Phe Asp Leu Arg Asp Lys Arg Gln Arg Pro Gly Arg
 50                  55                  60

Asn Pro Lys Thr Gly Glu Glu Ile Pro Ile Thr Ala Arg Arg Val Val
 65                  70                  75                  80

Thr Phe Arg Pro Gly Gln Lys Leu Lys Ala Arg Val Glu Ala Tyr Ala
                 85                  90                  95

Gly Thr Lys Ser
            100

<210> SEQ ID NO 7
<211> LENGTH: 6
<212> TYPE: PRT
<213> ORGANISM: Unknown
<220> FEATURE:
<221> NAME/KEY: source
<223> OTHER INFORMATION: /note="Description of Unknown: Beta-3 portion
      of IHF-alpha peptide"

<400> SEQUENCE: 7

Thr Phe Arg Pro Gly Gln
  1               5

<210> SEQ ID NO 8
<211> LENGTH: 6
<212> TYPE: PRT
<213> ORGANISM: Unknown
<220> FEATURE:
<221> NAME/KEY: source
<223> OTHER INFORMATION: /note="Description of Unknown: Beta-3 portion
      of IHF-alpha peptide"

<400> SEQUENCE: 8

His Phe Lys Pro Gly Lys
  1               5

<210> SEQ ID NO 9
<211> LENGTH: 6
<212> TYPE: PRT
<213> ORGANISM: Unknown
<220> FEATURE:
<221> NAME/KEY: source
<223> OTHER INFORMATION: /note="Description of Unknown: Beta-3 portion
      of IHF-alpha peptide"

<400> SEQUENCE: 9
```

```
Thr Phe Lys Pro Gly Gln
1               5
```

<210> SEQ ID NO 10
<211> LENGTH: 6
<212> TYPE: PRT
<213> ORGANISM: Unknown
<220> FEATURE:
<221> NAME/KEY: source
<223> OTHER INFORMATION: /note="Description of Unknown: Beta-3 portion
      of IHF-alpha peptide"

<400> SEQUENCE: 10

```
Thr Phe Lys Pro Gly Gln
1               5
```

<210> SEQ ID NO 11
<211> LENGTH: 6
<212> TYPE: PRT
<213> ORGANISM: Unknown
<220> FEATURE:
<221> NAME/KEY: source
<223> OTHER INFORMATION: /note="Description of Unknown: Beta-3 portion
      of IHF-alpha peptide"

<400> SEQUENCE: 11

```
Thr Phe Lys Pro Gly Gln
1               5
```

<210> SEQ ID NO 12
<211> LENGTH: 6
<212> TYPE: PRT
<213> ORGANISM: Unknown
<220> FEATURE:
<221> NAME/KEY: source
<223> OTHER INFORMATION: /note="Description of Unknown: Beta-3 portion
      of IHF-alpha peptide"

<400> SEQUENCE: 12

```
Thr Phe Arg Pro Gly Gln
1               5
```

<210> SEQ ID NO 13
<211> LENGTH: 6
<212> TYPE: PRT
<213> ORGANISM: Unknown
<220> FEATURE:
<221> NAME/KEY: source
<223> OTHER INFORMATION: /note="Description of Unknown: Beta-3 portion
      of IHF-alpha peptide"

<400> SEQUENCE: 13

```
Thr Phe Arg Pro Gly Gln
1               5
```

<210> SEQ ID NO 14
<211> LENGTH: 90
<212> TYPE: PRT
<213> ORGANISM: Escherichia coli

<400> SEQUENCE: 14

```
Met Asn Lys Thr Gln Leu Ile Asp Val Ile Ala Glu Lys Ala Glu Leu
1               5                   10                  15

Ser Lys Thr Gln Ala Lys Ala Ala Leu Glu Ser Thr Leu Ala Ala Ile
                20                  25                  30

Thr Glu Ser Leu Lys Glu Gly Asp Ala Val Gln Leu Val Gly Phe Gly
            35                  40                  45
```

Thr Phe Lys Val Asn His Arg Ala Glu Arg Thr Gly Arg Asn Pro Gln
            50                  55                  60

Thr Gly Lys Glu Ile Lys Ile Ala Ala Ala Asn Val Pro Ala Phe Val
65                  70                  75                  80

Ser Gly Lys Ala Leu Lys Asp Ala Val Lys
                85                  90

<210> SEQ ID NO 15
<211> LENGTH: 90
<212> TYPE: PRT
<213> ORGANISM: Escherichia coli

<400> SEQUENCE: 15

Met Asn Lys Ser Gln Leu Ile Asp Lys Ile Ala Ala Gly Ala Asp Ile
1               5                   10                  15

Ser Lys Ala Ala Ala Gly Arg Ala Leu Asp Ala Ile Ile Ala Ser Val
                20                  25                  30

Thr Glu Ser Leu Lys Glu Gly Asp Asp Val Ala Leu Val Gly Phe Gly
            35                  40                  45

Thr Phe Ala Val Lys Glu Arg Ala Ala Arg Thr Gly Arg Asn Pro Gln
            50                  55                  60

Thr Gly Lys Glu Ile Thr Ile Ala Ala Ala Lys Val Pro Ser Phe Arg
65                  70                  75                  80

Ala Gly Lys Ala Leu Lys Asp Ala Val Asn
                85                  90

<210> SEQ ID NO 16
<211> LENGTH: 6
<212> TYPE: PRT
<213> ORGANISM: Unknown
<220> FEATURE:
<221> NAME/KEY: source
<223> OTHER INFORMATION: /note="Description of Unknown: Beta-3 portion
      of IHF-alpha peptide"

<400> SEQUENCE: 16

Ala Phe Val Ser Gly Lys
1               5

<210> SEQ ID NO 17
<211> LENGTH: 6
<212> TYPE: PRT
<213> ORGANISM: Unknown
<220> FEATURE:
<221> NAME/KEY: source
<223> OTHER INFORMATION: /note="Description of Unknown: Beta-3 portion
      of IHF-alpha peptide"

<400> SEQUENCE: 17

Ser Phe Arg Ala Gly Lys
1               5

<210> SEQ ID NO 18
<211> LENGTH: 20
<212> TYPE: PRT
<213> ORGANISM: Escherichia coli

<400> SEQUENCE: 18

Thr Phe Arg Pro Gly Gln Lys Leu Lys Ser Arg Val Glu Asn Ala Ser
1               5                   10                  15

Pro Lys Asp Glu
            20

```
<210> SEQ ID NO 19
<211> LENGTH: 20
<212> TYPE: PRT
<213> ORGANISM: Escherichia coli

<400> SEQUENCE: 19

Lys Tyr Val Pro His Phe Lys Pro Gly Lys Glu Leu Arg Asp Arg Ala
1               5                   10                  15

Asn Ile Tyr Gly
            20

<210> SEQ ID NO 20
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: modified_base
<222> LOCATION: (7)..(10)
<223> OTHER INFORMATION: a, c, t, g, unknown or other

<400> SEQUENCE: 20
watcaannnn ttr                                                              13

<210> SEQ ID NO 21
<211> LENGTH: 12
<212> TYPE: PRT
<213> ORGANISM: Escherichia coli

<400> SEQUENCE: 21

Gly Arg Asn Pro Lys Thr Gly Glu Asp Ile Pro Ile
1               5                   10

<210> SEQ ID NO 22
<211> LENGTH: 12
<212> TYPE: PRT
<213> ORGANISM: Escherichia coli

<400> SEQUENCE: 22

Gly Arg Asn Pro Lys Thr Gly Asp Lys Val Glu Leu
1               5                   10

<210> SEQ ID NO 23
<211> LENGTH: 12
<212> TYPE: PRT
<213> ORGANISM: Escherichia coli

<400> SEQUENCE: 23

Gly Arg Asn Pro Gln Thr Gly Lys Glu Ile Lys Ile
1               5                   10

<210> SEQ ID NO 24
<211> LENGTH: 12
<212> TYPE: PRT
<213> ORGANISM: Escherichia coli

<400> SEQUENCE: 24

Gly Arg Asn Pro Gln Thr Gly Lys Glu Ile Thr Ile
1               5                   10

<210> SEQ ID NO 25
```

```
<211> LENGTH: 14
<212> TYPE: PRT
<213> ORGANISM: Unknown
<220> FEATURE:
<221> NAME/KEY: source
<223> OTHER INFORMATION: /note="Description of Unknown: alpha-3 portion
      of IHF-alpha peptide"

<400> SEQUENCE: 25

Lys Leu Lys Ser Arg Val Glu Asn Ala Ser Pro Lys Asp Glu
1               5                   10

<210> SEQ ID NO 26
<211> LENGTH: 10
<212> TYPE: PRT
<213> ORGANISM: Unknown
<220> FEATURE:
<221> NAME/KEY: source
<223> OTHER INFORMATION: /note="Description of Unknown: alpha-3 portion
      of IHF-alpha peptide"

<400> SEQUENCE: 26

Glu Leu Arg Asp Arg Ala Asn Ile Tyr Gly
1               5                   10

<210> SEQ ID NO 27
<211> LENGTH: 10
<212> TYPE: PRT
<213> ORGANISM: Unknown
<220> FEATURE:
<221> NAME/KEY: source
<223> OTHER INFORMATION: /note="Description of Unknown: alpha-3 portion
      of IHF-alpha peptide"

<400> SEQUENCE: 27

Lys Leu Arg Ala Arg Val Glu Lys Thr Lys
1               5                   10

<210> SEQ ID NO 28
<211> LENGTH: 10
<212> TYPE: PRT
<213> ORGANISM: Unknown
<220> FEATURE:
<221> NAME/KEY: source
<223> OTHER INFORMATION: /note="Description of Unknown: alpha-3 portion
      of IHF-alpha peptide"

<400> SEQUENCE: 28

Lys Leu Arg Ala Arg Val Glu Asn Thr Lys
1               5                   10

<210> SEQ ID NO 29
<211> LENGTH: 10
<212> TYPE: PRT
<213> ORGANISM: Unknown
<220> FEATURE:
<221> NAME/KEY: source
<223> OTHER INFORMATION: /note="Description of Unknown: alpha-3 portion
      of IHF-alpha peptide"

<400> SEQUENCE: 29

Lys Leu Arg Ala Arg Val Glu Lys Thr Lys
1               5                   10

<210> SEQ ID NO 30
<211> LENGTH: 14
<212> TYPE: PRT
<213> ORGANISM: Unknown
<220> FEATURE:
```

```
<221> NAME/KEY: source
<223> OTHER INFORMATION: /note="Description of Unknown: alpha-3 portion
      of IHF-alpha peptide"

<400> SEQUENCE: 30

Lys Leu Lys Ser Arg Val Glu Asn Ala Ser Pro Lys Asp Glu
1               5                   10

<210> SEQ ID NO 31
<211> LENGTH: 14
<212> TYPE: PRT
<213> ORGANISM: Unknown
<220> FEATURE:
<221> NAME/KEY: source
<223> OTHER INFORMATION: /note="Description of Unknown: alpha-3 portion
      of IHF-alpha peptide"

<400> SEQUENCE: 31

Lys Leu Lys Ala Arg Val Glu Ala Tyr Ala Gly Thr Lys Ser
1               5                   10

<210> SEQ ID NO 32
<211> LENGTH: 7
<212> TYPE: PRT
<213> ORGANISM: Unknown
<220> FEATURE:
<221> NAME/KEY: source
<223> OTHER INFORMATION: /note="Description of Unknown: alpha-3 portion
      of IHF-alpha peptide"

<400> SEQUENCE: 32

Ala Leu Lys Asp Ala Val Lys
1               5

<210> SEQ ID NO 33
<211> LENGTH: 7
<212> TYPE: PRT
<213> ORGANISM: Unknown
<220> FEATURE:
<221> NAME/KEY: source
<223> OTHER INFORMATION: /note="Description of Unknown: alpha-3 portion
      of IHF-alpha peptide"

<400> SEQUENCE: 33

Ala Leu Lys Asp Ala Val Asn
1               5
```

PROBIOTIC FORMULATIONS AND METHODS FOR USE

CROSS-REFERENCE TO RELATED APPLICATIONS

This application is a continuation application of U.S. application Ser. No. 15/257,673, filed Sep. 6, 2016, which claims priority to continuation under 35 U.S.C. § 120 of International Application No. PCT/US2015/019059, filed Mar. 5, 2015, which in turn claims priority under 35 U.S.C. § 119(e) to U.S. Provisional Application No. 61/949,058, filed Mar. 6, 2014, the content of each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 26, 2015, is named 106887-0160_SL.txt and is 13,545 bytes in size.

FIELD OF THE INVENTION

This disclosure relates to novel probiotic formulations and methods for using same for treating or preventing disease.

BACKGROUND

Diarrheal illness is a major worldwide cause of morbidity and mortality, and accounts for approximately 15% of deaths in children. Enterohemorrhagic *Escherichia coli* (EHEC) and enteropathogenic *E. coli* (EPEC) are two primary bacterial causes of pediatric diarrhea. The mechanisms by which these pathogens cause diarrheal disease is not yet completely understood, but is initiated when the pathogens colonize the intestinal epithelium (Nataro and Kaper (1998) Clin Microbiol Rev. 11:142-201).

A closely related pathogen, namely *Citrobacter rodentium* is a murine pathogen that is widely used to model human EPEC and EHEC infection, because mice are relatively resistant to both EPEC and EHEC. In mice, *C. rodentium* results in colonic pathology that is nearly indistinguishable from that produced by EPEC and EHEC in humans (Borenshtein, M. et al. (2008) Curr Opin Gastroenterol. 24:32-37; Luperchio and Schauer (2001) Microbes Infect. 3:333-40; Mundy, T.T. et al. (2005) Cell Microbiol. 7:1697-706). This may not be surprising, since *C. rodentium* possesses a homologue of the locus of enterocyte effacement (LEE) pathogenicity island carried by EPEC and EHEC that encodes for the effector proteins necessary for the development of attaching and effacing (A/E) lesions. These lesions are accompanied by the development of colonic hyperplasia, and pathological colitis marked by epithelial defects and leukocyte infiltration (Luperchio and Schauer (2001) Microbes Infect. 3:333-340).

The intestinal epithelium provides a formidable barrier to enteric pathogens. In order to cause disease, enteric pathogens must either adhere to or penetrate/invade host epithelial cells. Thus, interaction with epithelial cells is the first step in pathogenicity for all enteric pathogens, and this step can be studied through the use of A/E pathogens by assessing colonic colonization and resultant pathology.

Colonization of A/E pathogens in the colon is dependent upon the composition of the intestinal microbiota. Inducing dysbiosis (the disruption of the native populations of beneficial bacteria) within the colonic microbiota by administering antibiotics (Wlodarska, B. et al. (2011) Infect Immun. 79:1536-45) or by inducing an inflammatory response (Lupp, M. L. et al. (2007) Cell Host Microbe 2:119-129) has been shown to greatly enhance pathogen colonization.

Colonic dysbiosis can further exacerbate the inflammatory response to the colonic pathogen (Wlodarska, B. et al. (2011) Infect Immun. 79:1536-1545), but even in the absence of pathogen challenge, dysbiosis can propagate inflammatory responses in genetically susceptible individuals, as evidenced by the findings of dysbiosis in patients with inflammatory bowel disease (Machiels et al. (2013) Gut, published online first Sep. 10, 2013; Morgan et al. (2012) Genome Biol. 13:R79) or irritable bowel syndrome (Carroll et al. (2012) Neurogastroenterol Motil. 24:521-30, e248; Chassard, M. et al. (2012) Aliment Pharmacol Ther. 35:828-838).

Probiotics, are live microbes that when ingested in high enough quantities confer a health benefit for the host (Food and Agriculture Organization of the United Nations and World Health Organization, "Health and Nutritional Properties of Probiotics in Food Including Powdered Milk with Live Bacteria" (2001)), are gaining traction as a viable option for treating enteric diseases (Hemarajata and Versalovic (2013) Therap Adv Gastroenterol. 6:39-51).

Many probiotic microbes have the capacity to enhance immune system activity, but fewer probiotic microbes have anti-inflammatory effects. *Lactobacillus reuteri* is a commonly used probiotic that has been shown to regulate the mammalian and avian intestinal immune system (Lin et al. (2008) Inflamm Bowel Dis. 14:1068-1083). Studies in vitro demonstrate that some strains of *L. reuteri* (such as PTA6475) can suppress the ability of myeloid cells to produce inflammatory cytokines (such as TNF-α) through a down-regulation of cell signal transduction pathways (e.g., c-Jun-dependent activator protein 1 (AP-1)) (Jones and Versalovic (2009) BMC Microbiol. 9:35; Lin et al. (2008) Inflamm Bowel Dis. 14:1068-1083).

Other strains of *L. reuteri*, such as ATCC23272, can down-regulate both cytokine and chemokine production by colonic epithelial cells stimulated with *C. rodentium*. *L. reuteri* can also reduce colonic inflammation in both juvenile and adult animals (Eaton, A. et al. (2011) Infect Immun. 79:185-191; Schreiber et al. (2009) Am J Physiol Gastrointest Liver Physiol. 296:G534-G542).

Studies demonstrate that *L. reuteri* attenuates the exacerbating effects of stress on *C. rodentium*-induced colitis as marked by reductions in colonic cytokines and chemokines, inflammatory cell infiltration, colonic epithelial cell defects, and pathogen translocation from the colon to the spleen (Mackos et al. (2013) Infection, Infect Immun. 81:3253-3263).

The effects of *L. reuteri* are most evident when stress leads to mild to moderate *C. rodentium*-induced colitis. However, under stress conditions that lead to severe *C. rodentium*-induced colitis, *L. reuteri* was able to prevent pathogen translocation and the development of systemic inflammatory responses, but it was not able to reduce all aspects of colonic pathology (Mackos et al. (2013) Infection, Infect Immun. 81:3253-3263).

Moreover, the effects of *L. reuteri* on the host were short-lived and no longer evident after daily administration was terminated. These studies demonstrate the immunomodulatory potential of *L. reuteri*.

SUMMARY

Under the right conditions, many probiotics can effectively prevent pathogen colonization due to either direct (e.g., production of antimicrobial defenses) or indirect (e.g., stimulation of host defenses) mechanisms. Few probiotic species are able to both prevent pathogen colonization and limit excessive inflammatory responses. This is important, however, because excessive colonic inflammation in response to colonic infection can lead to the development of protracted illness, such as post-infectious irritable bowel syndrome. Thus, the development of probiotics that are able to prevent excessive immune responses to colonic pathogens, while still maintaining anti-bacterial immunity would have the ability to prevent both short-term and longer-term health effects of enteric infection.

Anxiety and depression are common co-morbidities in both adults and children with gastrointestinal disease (Maunder et al. (2008) Curr Mol Med. 8:247-252; Waler et al. (2008) Am J Gastroenterol. 103:1989-1997), and studies suggest that reducing gastrointestinal disease can in turn improve anxiety and depression (Guloksuz et al. (2013) PLoS One 8(3):e6043).

Aspects and embodiments of this technology combine the probiotic bacteria with prebiotic substances to help stimulate the exclusive growth of the probiotic species and provide the bacteria in the form of a biofilm on a biocompatible microsphere, which has greater efficacy and duration. It has been shown that probiotic biofilms can be grown on surfaces as a means to introduce bacteria into the site of wounds, where a formulation comprising a plaster or dressing based on a hydrocolloid that is a natural gelatin to treat wounds (i.e., EP2450062). However, there is an unmet need for fewer probiotic doses and greater efficacy of probiotic bacteria and its appropriate formulation in the methods as disclosed herein, to the best of Applicants' knowledge, has not yet heretofore been disclosed.

This technology provides methods of formulation, which enhance the efficiency and durability of introducing probiotic strains at a site. It specifically bypasses the rate limiting step of biofilm formation. This technology is useful for gastrointestinal gut health and any aspects where probiotic bacteria need to establish, e.g., the gastrointestinal tract, wound healing, skin, vaginal, oral, water purification.

Probiotics are a natural way to protect and restore gut microbiota to a healthy state. Unfortunately, even under optimal conditions, probiotic bacteria (as typically delivered) fail to establish, or sufficiently persist, minimizing the magnitude and duration of their healthful effects. One of the rate limiting steps is the capacity of introduced bacteria to form a lasting biofilm. When bacteria are already in the form of a biofilm (a surface adhered community) as opposed to planktonic (free-living), they more readily establish and persist. The positive effects of probiotic bacteria can be enhanced by providing them in a biofilm state; this can readily be accomplished by growing the bacteria on the surface of a biocompatible and non-toxic microsphere. Biocompatible microspheres can be biodegradable polymers, non-biodegradable polymers, a metal, or a combination thereof. When this surface is in the form of a microsphere, prebiotic and/or prebiofilmic substances can be added as cargo to facilitate establishment and maintenance of the probiotic bacterial biofilm.

Microspheres have added value in ideally providing diffusible prebiotic (nutritional supplementation specific/exclusive to probiotic bacteria) cargo that can help promote probiotic bacterial establishment and survival while limiting pathogenic bacterial challenge. At least for the probiotic bacterium *Lactobacillus reuteri*, the biofilm state is advantageous in establishing in the murine gut over the same bacteria in planktonic form.

Furthermore, *L. reuteri* introduced into mice as biofilms have a more robust and durable prophylactic effect on the pathogenesis of the enteropathogenic bacterium, *Citrobacter rodentium*, than *L. reuteri* in its planktonic form. Based on these results, highly integrated examples are developed that yield novel formulations of probiotics that provide greater and more lasting effects against dysbiosis preventing or even treating gut pathogenesis with a far reduced need for patient compliance.

The biofilm-generating probiotic bacterium adheres to the surface of the biocompatible microsphere and generates a biofilm. The biocompatible microsphere has either a solid or hollow core. When the biocompatible microsphere has a hollow core, it can carry a prebiotic and any nutritional supplementation for the probiotic bacterium as a cargo. The prebiotic can be encapsulated within the hollow core. The microsphere can also carry a drug, or a compound, or an agent, which is selective against a pathogen, that in one aspect, may compete with the health-inducing bacterium in the composition. In addition to a biocompatible microsphere, biofilm-generating probiotic and prebiotic, a novel probiotic formulation can also contain a prebiofilmic, which is a substance that supports biofilm formation and/or durability, and in one aspect, the prebiofilmic is a DNA binding polypeptide or protein and/or a DNABII polypeptide or protein or a fragment thereof that supports biofilm formation and/or durability.

In view of the above advantages, provided herein is a composition comprising, or alternatively consisting essentially of, or yet further consisting of, a biocompatible microsphere, a biofilm-generating probiotic bacterium and a prebiotic, wherein the prebiotic comprises, or alternatively consisting essentially of, or yet consisting of, a nutritional supplementation for the probiotic bacterium. In one aspect, the composition further comprises, or alternatively consists essentially of, or yet further consisting of, a carrier, such as a pharmaceutically acceptable carrier or a biocompatible scaffold.

In some embodiments, the composition is formulated in a dosage form. Suitable dosage forms include, but are not limited to a suppository, a powder, a liquid, a capsule, a chewable tablet, a swallowable tablet, a buccal tablet, a troche, a lozenge, a soft chew, a solution, a suspension, a spray, a tincture, a decoction, an infusion, and combinations thereof.

This disclosure also provides a method for preparing the above-noted composition, the method comprising, or alternatively consisting essentially of, or yet further consisting of, admixing a biocompatible microsphere with a biofilm-generating probiotic bacterium, a prebiotic, and in one aspect, further admixing a prebiofilmic. In a further aspect, the method further comprises, or alternatively consists essentially of, or yet further consists of, admixing an effective amount of a nutritional supplement for the probiotic bacterium.

This disclosure also provides a composition comprising, or alternatively consisting essentially of, or yet further consisting of, a PGLA-biocompatible microsphere, one or more biofilm-generating probiotic bacterium comprising at least *Lactobacillus reuteri* ("*L. reuteri*"), and a nutritional supplementation comprising one or more of sucrose, glycerol, fructose and/or maltose, in an amount to support the growth of the probiotic bacterium. The composition may further comprise, or alternatively consisting essentially of, or yet further consist of, an effective amount of an HU polypeptide or protein. The composition can further comprise a pharmaceutically acceptable carrier or a biocompatible scaffold and is optionally formulated as a suppository.

This disclosure also provides a method for treating or preventing a disease suitable treated by a biofilm in a subject, such as inflammatory bowled disease, necrotizing enterocolitis (NEC) or psychological disorders or mood disorders, in a subject comprising, or alternatively consisting essentially of, or yet further consisting of, administering to a subject in need thereof, an effective amount of a composition comprising, or alternatively consisting essentially of, or yet further consisting of, a composition as described herein.

In some embodiments, a kit is provided comprising, or alternatively consisting essentially of, or yet consisting of, a composition as described herein and instructions for use diagnostically or therapeutically.

SEQUENCE LISTING

Figure 1A:
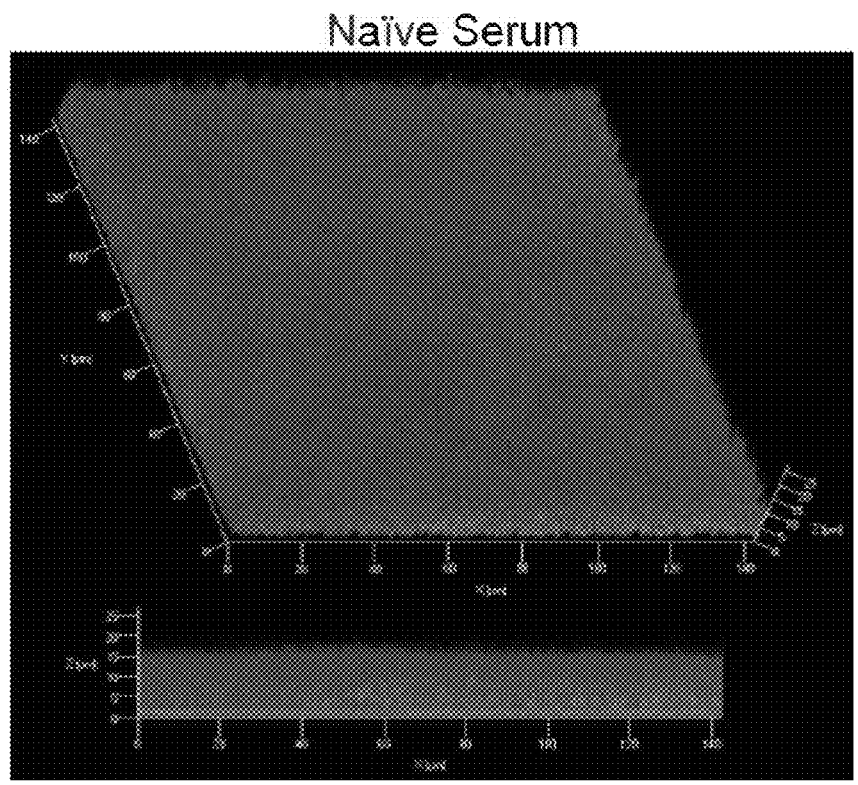
FIGS. 1A and 1B illustrate that *L. reuteri* biofilm structural integrity relies on the presence of DNABII family proteins. Confocal microscopy images of in vitro *L. reuteri* biofilms stained with LIVE/DEAD BacLight Bacterial Viability Kit (Molecular Probes). *L. reuteri* biofilms were grown for 24 hours at 37° C. and 5% CO2, at which time they were treated with a 1:50 dilution of either A) rabbit naïve serum, B) rabbit anti-integration host factor polypeptide ("IHF"), or media with nothing added (data not shown) for 16 hours. Anti-IHF treatments resulted in a 20% decrease in maximum height, 35% decrease in average thickness, and 41% decrease in biomass (data not shown).
Figure 1B:
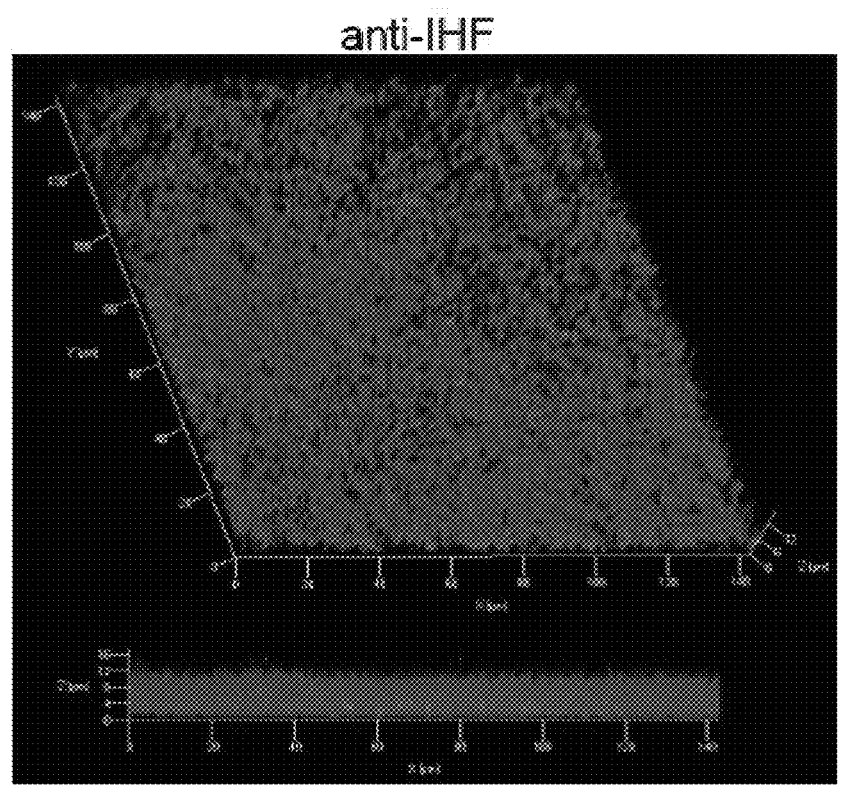
Figure 2:
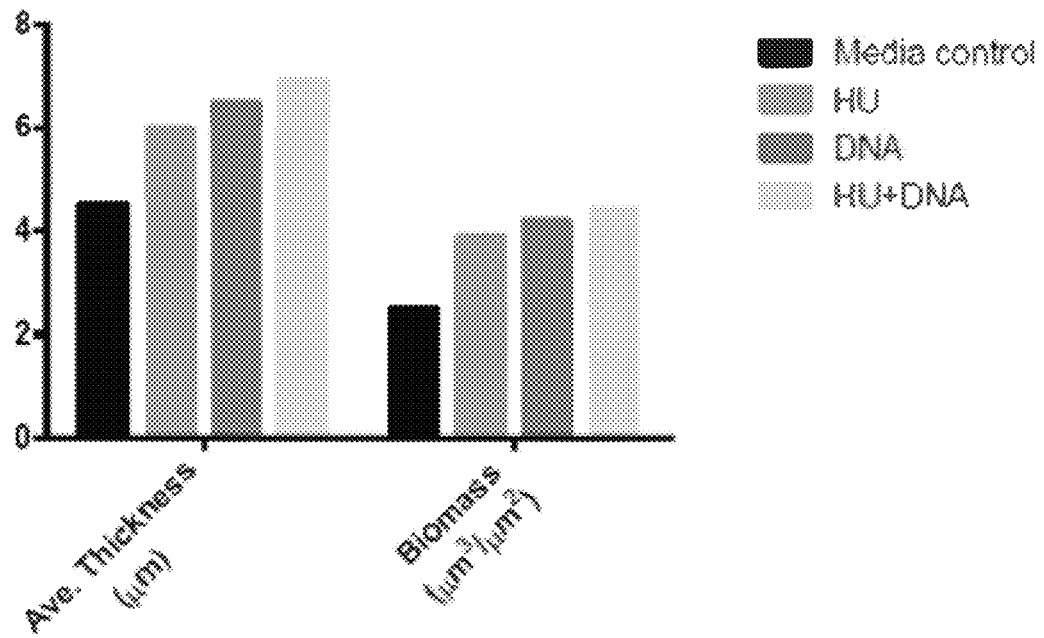
FIG. 2 illustrates that Prebiotic compounds increase probiotic biofilms in average thickness and biomass. Addition of 10 μg/ml *S. mutans* HU to *L. reuteri* biofilm at time of seeding increased average thickness and biomass 33%, and 55%, respectively. Addition of 10 μg/ml calf thymus DNA increased average thickness 44% and biomass 68%. Adding 10 μg/ml of HU and DNA together led to an increased effect compared to either alone, with average thickness increasing 53% and biomass increasing 78%.

SEQ ID NO: 1 Full Length Wild type (wt) 86-028NP *Haemophilus influenzae* IhfA; Genbank accession No.: AAX88425.1, last accessed Mar. 21, 2011:
MATITKLDIIEYLSDKYHLSK

QDTKNVVENFLEEIRLSLESGQDVKLSGFGNFELRDKSSRPGRNPKTG

DVVPVSARRVVTFKPGQKLRARVEKTK

SEQ ID NO: 2 Full Length wild-type 86-028NP *Haemophilus influenzae* HU, Genbank accession No.: YP_248142.1, last accessed Mar. 21, 2011:
MRFVTIFINHAFNSSQVRLSFAQFLR

QIRKDTFKESNFLFNRRYKFMNKTDLIDAIANAAELNKKQAKAALEAT

LDAITASLKEGEPVQLIGFGTFKVNERAARTGRNPQTGAEIQIAASKV

PAFVSGKALKDAIK

SEQ ID NO: 3 Full Length wt R2846 *Haemophilus influenzae* IhfA, Genbank accession No.: ADO96375, last accessed Mar. 21, 2011:
MATITKLDIIEYLSDKYHLSKQDTKNVVENFL

EEIRLSLESGQDVKLSGFGNFELRDKSSRPGRNPKTGDVVPVSARRVV

TFKPGQKLRARVEKTK

SEQ ID NO: 4 Full Length wild-type Rd *Haemophilus influenzae* IhfA; Genbank accession No.: AAC22959.1, last accessed Mar. 21, 2011:
MATITKLDIIEYLSDKYHLSKQDTK

NVVENFLEEIRLSLESGQDVKLSGFGNFELRDKSSRPGRNPKTGDVVP

VSARRVVTFKPGQKLRARVEKTK;

SEQ ID NO: 5 Full Length wild-type *E. coli* K12 IhfA; Genbank accession No.: AAC74782.1, last accessed Mar. 21, 2011:
MALTKAEMSEYLFDKLGLSKRDAKELVELFFE

EIRRALENGEQVKLSGFGNFDLRDKNQRPGRNPKTGEDIPITARRVVT

FRPGQKLKSRVENASPKDE;
DNA Genbank No. NC_000913

SEQ ID NO: 6 Full Length wild-type *P. aeruginosa* PA 01 IhfA; Genbank accession No.: AAG06126.1, last accessed Mar. 21, 2011:
MGALTKAEIAERLYEELGLNKREA

KELVELFFEEIRQALEHNEQVKLSGFGNFDLRDKRQRPGRNPKTGEEI

PITARRVVTFRPGQKLKARVEAYAGTKS

SEQ ID NOS: 7 and 25, respectively, in order of appearance: β-3 and α-3 portions of (IHFα):
TFRPGQ
and

KLKSRVENASPKDE

SEQ ID NOS: 8 and 26, respectively, in order of appearance: β-3 and α-3 portions of (IHFβ):
HFKPGK
and

ELRDRANIYG

SEQ ID NOS: 9 and 27, respectively, in order of appearance: β-3 and α-3 portions of:
TFKPGQ
and

KLRARVEKTK

SEQ ID NOS: 10 and 28, respectively, in order of
appearance: β-3 and α-3 portions of 2019
Haemophilus influenzae IhfA:
TFKPGQ
and

KLRARVENTK

SEQ ID NOS: 11 and 29, respectively, in order of
appearance: β-3 and α-3 portions of:
TFKPGQ
and:

KLRARVEKTK

SEQ ID NOS: 12 and 30, respectively, in order of
appearance: β-3 and α-3 portions of:
TFRPGQ
and

KLKSRVENASPKDE

SEQ ID NOS: 13 and 31, respectively, in order of
appearance: β-3 and α-3:
TFRPGQ
and

KLKARVEAYAGTKS

SEQ ID NO: 14 E. coli hupA, Genbank accession
No.: AP_003818, Last accessed Mar. 21, 2011:
MNKTQLIDVIAEKAELSKTQAKAALESTLAAITESLKEGDAVQLVGFG

TFKVNHRAERTGRNPQTGKEIKIAAANVPAFVSGKALKDAVK

SEQ ID NO: 15 E. coli hupB, Genbank accession
No.: AP_001090.1, Last accessed Mar. 21,2011:
MNKSQLIDKIAAGADISKAAAGRALDAIIASVTESLKEGDDVALVGFG

TFAVKERAARTGRNPQTGKEITIAAAKVPSFRAGKALKDAVN

SEQ ID NOS: 16 and 32, respectively, in order of
appearance: β-3 and α-3 portions of:
AFVSGK
and

ALKDAVK

SEQ ID NOS: 17 and 33, respectively, in order of
appearance: β-3 and α-3 portions of
SFRAGK
and

ALKDAVN

SEQ ID NO: 18 C-terminal 20 amino acids of
IHF α:
TFRPGQKLKSRVENASPKDE

SEQ ID NO: 19 C-terminal 20 amino acids of
IHF β:
KYVPHFKPGKELRDRANIYG

SEQ ID NO: 20 DNABII binding consensus sequence:
WATCAANNNNTTR
wherein W is A or T, N is any base and R is a
purine.

SEQ ID NO: 21 E. coli IHFalpha:
GRNPKTGEDIPI

SEQ ID NO: 22 E. coli IHFbeta:
GRNPKTGDKVEL

SEQ ID NO: 23 E. coli HUalpha:
GRNPQTGKEIKI

SEQ ID NO: 24 E. coli HUbeta:
GRNPQTGKEITI

DETAILED DESCRIPTION

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All technical and patent publications cited herein are incorporated herein by reference in their entirety. Nothing herein is to be construed as an admission that the invention is not entitled to antedate such disclosure by virtue of prior invention.

The practice of the present technology will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration and molecular weight, including ranges, are approximations which are varied (+) or (−) by increments of 1.0 or 0.1, as appropriate, or alternatively by a variation of +/−15%, or alternatively 10%, or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a bacterium" includes a plurality of bacteria, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention. Embodiments defined by each of these transition terms are within the scope of this invention.

A "biofilm" intends a thin layer or an organized community of microorganisms that at times can adhere to the surface of a structure, that may be organic or inorganic, together with the polymers, such as DNA, that they secrete and/or release. The biofilms are very resistant to microbiotics and antimicrobial agents. They live on gingival tissues, teeth, and restorations, causing caries and periodontal disease, also known as periodontal plaque disease. They also cause chronic middle ear infections. Biofilms can also form on the surface of dental implants, stents, catheter lines and contact lenses. They grow on pacemakers, heart valve replacements, artificial joints and other surgical implants. The Centers for Disease Control estimate that over 65% of nosocomial (hospital-acquired) infections are caused by biofilms. Fungal biofilms also frequently contaminate medical devices. They cause chronic vaginal infections and lead to life-threatening systemic infections in people with hobbled immune systems. Biofilms also are involved in numerous diseases. For instance, cystic fibrosis patients have Pseudomonas infections that often result in antibiotic resistant biofilms.

A "prebiotic" intends a nutritional supplement for the probiotic bacterium. Prebiotics are food ingredients, for example, oligosaccharides, that are non-digestible by a subject (e.g., by a mammal such as a human), and that stimulates the growth or activity of one or more beneficial bacteria and/or inhibit the growth or activity of one or more pathogenic bacteria. A prebiotic may selectively stimulate the growth and/or activity of one or a limited number of bacteria in the subject.

A "prebiofilmic" intends a substance that supports biofilm formation and durability, for example the prebiofilmic can be a substance that supports the extracellular matrix of the biofilm like an eDNA binding polypeptide or protein or alternatively a substrate that can be converted into a substance that facilitate adhesion, e.g. sucrose.

A "DNABII polypeptide or protein" intends a DNA binding protein or polypeptide that is composed of DNA-binding domains and thus have a specific or general affinity for DNA. In one aspect, they bind DNA in the minor grove. Non-limiting examples of DNABII proteins are an integration host factor (IHF) protein and a histone-like protein from E. coli strain U93 (HU), examples of which are provided in SEQ ID NOs: 1 to 24 and additional strains and polypeptides are provided in Table 4. Also intended are polypeptide fragments and equivalent polypeptides that have amino acid modifications that do not substantially change the biological activity of the protein or polypeptides, or active fragment thereof. Active fragments thereof include, for example, the c-terminal half or c-terminal third of the protein or polypeptide. Other DNA binding proteins that can be associated with the biofilm include DPS (Genbank Accession No.: CAA49169), H-NS (Genbank Accession No.: CAA47740), Hfq (Genbank Accession No.: ACE63256), CbpA (Genbank Accession No.: BAA03950) and CbpB (Genbank Accession No.: NP_418813), as well as equivalent polpyeptides and active fragments thereof.

A "microsphere" intends a biofilm-carrying and/or compound-carrying (e.g., drug-carrying) particulate or granular material within the particular size range recited. As used herein, a microsphere consisting of particles 50 millimeters or less in diameter, and 1 micron or more (e.g., 1 to 100 or alternatively, or alternatively, 1 to 75 microns, or alternatively 1 to 50, or alternatively 1 to 25, or alternatively 1 to 10 microns) in diameter. Non-limiting examples of such include hollow microspheres that can, in some aspects, contain a pharmaceutical or drug, microcapsules (in which the excipient forms a skin or shell that surrounds and contains a cargo, such as a drug), and microparticles, which are used as a generic term for any particles in the recited size range, whether spherical or not, as those terms are typically used in the art.

A "biodegradable polymer" intends polymers that are biocompatible and can degrade in vivo by bodily processes to products that are readily disposable by the body and should not accumulate in the body.

By "biocompatible", it is meant that the components of the delivery system will not cause tissue injury or injury to the human biological system. To impart biocompatibility, polymers and excipients that have had history of safe use in humans or with GRAS (Generally Accepted As Safe) status, are preferentially used. By biocompatibility, it is meant that the ingredients and excipients used in the composition will ultimately be "bioabsorbed" or cleared by the body with no adverse effects to the body. For a composition to be biocompatible, and be regarded as non-toxic, it must not cause toxicity to cells. Similarly, the term "bioabsorbable" refers to microspheres made from materials which undergo bioabsorption in vivo over a period of time such that long term accumulation of the material in the patient is avoided. The biocompatible nanoparticle is bioabsorbed over a period of less than 2 years, preferably less than 1 year and even more preferably less than 6 months. The rate of bioabsorption is related to the size of the particle, the material used, and other factors well recognized by the skilled artisan. A mixture of bioabsorbable, biocompatible materials can be used to form the microspheres used in this invention.

An "integration host factor" or "IHF" protein is a bacterial protein that is used by bacteriophages to incorporate their DNA into the host bacteria. These are DNA binding proteins that function in genetic recombination as well as in transcription and translational regulation. They also bind extracellular microbial DNA. The genes that encode the IHF protein subunits in E. coli are himA (Genbank accession No.: POA6X7.1) and himD (POA6Y1.1) genes. Non-limiting examples of such are provided in the attached sequence listing and noted in Table 4.

"HU" or "histone-like protein from E. coli strain U93" refers to a class of heterodimeric proteins typically associated with E. coli. HU proteins are known to bind DNA junctions. Related proteins have been isolated from other microorganisms. The complete amino acid sequence of E. coli HU was reported by Laine et al. (1980) Eur. J. Biochem. 103(3):447-481. Antibodies to the HU protein are commercially available from Abcam. Non-limiting examples of such are provided in the attached sequence listing.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

A "c-terminal polypeptide" intends the c-terminal half or c-terminal third of a polypeptide. As an example, for polypeptides containing 90 amino acids, the c-terminal polypeptide would comprise amino acids 46 through 90 or amino acids 60 through 90. In another aspect, the term intends the c-terminal 20 amino acids from the carboxy terminus.

A "n-terminal polypeptide" intends the n-terminal half of a polypeptide. As an example, for polypeptides containing 90 amino acids, the c-terminal polypeptide would comprise amino acids 1 through 45. In another aspect, the term intends the c-terminal 20 amino acids from the amino terminus.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides, antibodies and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

It is to be inferred without explicit recitation and unless otherwise intended, that when the present invention relates to a polypeptide, protein, polynucleotide or antibody, an equivalent or a biologically equivalent of such is intended within the scope of this invention. As used herein, the term "biological equivalent thereof" is intended to be synonymous with "equivalent thereof" when referring to a reference protein, antibody, polypeptide, polynucleotide or nucleic acid, intends those having minimal homology while still maintaining desired structure or functionality. Unless specifically recited herein, it is contemplated that any nucleic acid, polynucleotide, polypeptide or protein mentioned herein also includes equivalents thereof. For example, an equivalent intends at least about 70%, or alternatively 80% homology or identity and alternatively, at least about 85%, or alternatively at least about 90%, or alternatively at least about 95%, or alternatively 98% percent homology or identity across the protein or a particular fragment thereof, and exhibits substantially equivalent biological activity to the reference protein, polypeptide or nucleic acid.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

A "subject" or "patient" of diagnosis or treatment is a cell or an animal such as a mammal or a human. Non-human animals subject to diagnosis or treatment and are those subject to infections or animal models, for example, simians, murines, such as, rats, mice, chinchilla, canine, such as dogs, leporids, such as rabbits, livestock, sport animals and pets.

As used herein, the terms "treating," "treatment" and the like are used herein to mean obtaining a desired pharmacologic and/or physiologic effect. The effect may be prophylactic in terms of completely or partially preventing a disorder or sign or symptom thereof and/or may be therapeutic in terms of a partial or complete cure for a disorder and/or adverse effect attributable to the disorder.

To "prevent" intends to prevent a disorder or effect in vitro or in vivo in a system or subject that is predisposed to the disorder or effect. An example of such is preventing the formation of a biofilm in a system that is infected with a microorganism known to produce one.

The term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

"Pharmaceutically acceptable carriers" refers to any diluents, excipients or carriers that may be used in the compositions of the invention. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like and consistent with conventional pharmaceutical practices.

A "biocompatible scaffold" refers to a scaffold or matrix for with the ability to support biofilm proliferation upon administration to a subject. In other embodiments, a biocompatible scaffold is a precursor to an implantable device which has the ability to perform its intended function, with the desired degree of incorporation in the host, without eliciting an undesirable local or systemic effects in the host. Biocompatible scaffolds are described in U.S. Pat. Nos. 6,638,369 and 8,815,276.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include oral administration, vaginal, nasal administration, injection, topical application and by suppository.

The term "effective amount" refers to a quantity sufficient to achieve a beneficial or desired result or effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of a therapeutic composition, in some embodiments the effective amount is the amount sufficient to result in a protective response against a pathogen. In other embodiments, the effective amount is the amount sufficient to result in antibody generation against the antigen. In some embodiments, the effective amount is the amount required to confer passive immunity on a subject in need thereof. In some embodiments, the amount is sufficient to accomplish one or more of 1) clear pathogen; 2) restore healthy microbiota; 3) modulate the immune system; and 4) maintain metabolism and metabolic pathways.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The agents and compositions can be used in the manufacture of medicaments and for the treatment of humans and other animals by administration in accordance with conventional procedures, such as an active ingredient in pharmaceutical compositions.

An agent of the present invention can be administered for therapy by any suitable route of administration. It will also be appreciated that the preferred route will vary with the condition and age of the recipient and the disease being treated.

Necrotizing enterocolitis ("NEC") is a medical condition primarily seen in premature infants where portions of the bowel undergo necrosis (tissue death). It occurs postnatally (i.e., is not seen in stillborn infants) and is the second most common cause of mortality. 7% of all neonatal intensive care unit admissions are NEC related. The mortality rate is 12%.

Modes for Carrying Out the Disclosure

Diarrheal illness occurs in approximately four billion individuals per year and causes more than two million deaths worldwide. Among the most important bacterial causes of diarrheal illness in infants and young children are the attaching and effacing (A/E) pathogens, which upon colonization induce diarrheal disease that is associated with an increase in inflammatory cytokines and structural changes to colonic tissue. This acute infection can have a lasting effect on gut health, and infection with A/E pathogens and excessive inflammatory responses are known risk factors for the development of post-infectious irritable bowel syndrome.

Probiotics are a natural way to protect and restore gut microbiota to a healthy state and have been shown to promote health distal to the site of colonization. See Mackos et al. (2013) Infection and Immunity 81(9):3253-3262. Unfortunately, even under optimal conditions, probiotic bacteria fail to establish, or sufficiently persist, minimizing the magnitude and duration of their healthful effects. One of the rate limiting steps is the capacity of introduced bacteria to form a lasting biofilm. When bacteria are already in the form of a biofilm (a surface adhered community) as opposed to planktonic (free-living), they more readily establish and persist. The positive effects of probiotic bacteria can be enhanced by providing them in a biofilm state; this can readily be accomplished by growing the bacteria on the surface of a biocompatible and non-toxic microsphere. Biocompatible microspheres can be biodegradable polymers, non-biodegradable polymers, a metal, or a combination thereof. When this surface is in the form of a microsphere, prebiotic and/or prebiofilmic substances can be added as cargo to facilitate establishment and maintenance of the probiotic bacterial biofilm.

Microspheres have added value in ideally providing diffusible prebiotic (nutritional supplementation specific/exclusive to probiotic bacteria) cargo that can help promote probiotic bacterial establishment and survival while limiting pathogenic bacterial challenge. At least for the probiotic bacterium *Lactobacillus reuteri*, the biofilm state is advantageous in establishing in the murine gut over the same bacteria in planktonic form.

Furthermore, *L. reuteri* introduced into mice as biofilms have a more robust and durable prophylactic effect on the pathogenesis of the enteropathogenic bacterium, *Citrobacter rodentium*, than *L. reuteri* in its planktonic form. Based on these results, three highly integrated examples are developed that yield novel formulations of probiotics that provide greater and more lasting effects against dysbiosis preventing or even treating gut pathogenesis with a far reduced need for patient compliance.

The biofilm-generating probiotic bacterium adheres to the surface of the biocompatible microsphere and generates a biofilm. The biocompatible microsphere has either a solid or hollow core. When the biocompatible microsphere has a hollow core, it can carry a prebiotic and any nutritional supplementation for the probiotic bacterium as a cargo. The prebiotic can be encapsulated within the hollow core. The microsphere can also carry a drug, or a compound, or an agent, which is selective against the growth or proliferation of a pathogen. In addition to a biocompatible microsphere, biofilm-generating probiotic and prebiotic, a novel probiotic formulation may also contain a prebiofilmic, which a substance that supports biofilm formation and durability, specifically, the prebiofilmic is a DNA binding polypeptide or protein and/or a DNABII polypeptide or protein, a fragment and/or an equivalent of each thereof. Non-limiting examples of such are provided in the attached sequence listing. One or more drug, compound or agent as well as one or more prebiofilmic can be within a single microsphere.

The prebiotic can support the growth of any probiotic bacteria, including biofilm-generating bacteria. The prebiotic is usually one or more of a water-soluble carbohydrate, such as inulin, oligofructose, fructo-oligosaccharide, galacto-oligosaccharide, glucose, maltose, maltodextrins, polydextrose, sucrose, fructose, lactose, isomaltulose, polyols, and glycerol. The combination of various prebiotics can be used to support the growth of probiotics.

Probiotics are any type of micro-organisms that have health benefits. Probiotics are also commonly consumed as part of fermented foods with specially added active live cultures, such as in yogurt, soy yogurt, or as dietary supplements. Probiotics can also be taken as a suppository. Some limiting examples of probiotics are *L. acidophilus, L. crispatus, L. gasseri,* group *L. delbrueckii, L. salivarius, L. casei, L. paracasei, L. plantarum, L. rhamnosus, L. reuteri, L. brevis, L. buchneri, L. fermentum, L. rhamnosus, B. adolescentis, B. angulation, B. bifidum, B. breve, B. catenulatum, B. infantis, B. lactis, B. longum, B. pseudocatenulatum,* and *S. thermophiles.*

Probiotics support anti-bacterial immunity by preventing pathogen colonization and/or limiting excessive inflammatory responses. Without being bound by theory, the probiotics down-regulate cytokine and chemokine production.

The biocompatible microsphere can be one or more of a biodegradable polymer, a non-biodegradable polymer, a metal, or a mixture thereof. The biodegradable polymer can be selected from, but not limited to, poly(lactic-co-glycolic acid) or PLGA; polycaprolactone or PLC; Chitosan; Gelatin; DNA hydrogen; acetalated dextran; poly(lactide); poly(glycolide); poly(lactide-co-glycolide); poly(lactic acid); poly (glycolic acid); poly(lactic acid-co-glycolic acid); poly(lactide)/poly(ethylene glycol) copolymers; poly(glycolide)/poly(ethylene glycol) copolymer; poly(lactide-co-glycolide)/poly(ethylene glycol) copolymers; poly(lactic acid)/poly(ethylene glycol) copolymer; poly(glycolic acid)/poly(ethylene glycol) copolymer; poly(lactic acid-co-glycolic acid)/poly(ethylene glycol) copolymer; poly(caprolactone); poly(caprolactone)/poly(ethylene glycol) copolymer; poly(orthoester); poly(phosphazene); poly(hydroxybutyrate); poly(hydroxybutyrate); poly(lactide-co-caprolactone); polycarbonate; polyesteramide; polyanhidride; poly (dioxanone); poly(alkylene alkylate); polyethylene glycol/polyorthoester copolymer; polyurethane; poly(amino acid); polyetherester; polyacetal; polycyanoacrylate; poly(oxyethylene)/poly(oxypropylene) copolymer; Sephadex® copolymers (made from dextran cross-linked with epicholorhydine, commercially available from Sigma-Aldrich and noted in Koo and Wankat (1988) Korean Biochem. J. 21(1)) and/or a combination thereof. The non-biodegradable polymer can be selected from, but not limited to, poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof. The metal can be selected from, but not limited to, cobalt, chromium, gold, nickel, platinum, stainless steel, titanium, tantalum, nickel-titanium, and alloys and combinations thereof.

The microspheres are selected to facilitate the endurance and robustness of the probiotic biofilms are identified and characterized. It has been shown that probiotic biofilms formed on the biodegradable (and FDA approved) surface, poly(lactic-co-glycolic acid) (PLGA) yields biofilms that are superior at preventing pathogen translocation through the epithelial barrier. Other FDA approved or generally regarded as safe (GRAS) materials that can be used to create surfaces to grow biofilms are also examined. The results using biological effectiveness and durability in animal models and shelf life as the base criteria are prioritized. Finally, to further improve the effectiveness of the introduction and maintenance of the probiotic biofilm, prebiotic substances to the probiotic biofilm surface by way of diffusible cargo within the microspheres are provided.

Compositions

This disclosure provides a composition comprising, or alternatively consisting essentially of, or yet further consisting of, a biocompatible microsphere, a biofilm-generating probiotic bacterium and a prebiotic, wherein the prebiotic comprises, or alternatively consists essentially of, or yet further consists of a nutritional food source or supplement for the culturing and/or growth of the probiotic bacterium. The composition can further comprise a prebiofilmic. The prebiofilmic comprises a substance that supports biofilm formation and durability, specifically; the prebiofilmic can be a DNA binding polypeptide or protein and/or a DNABII polypeptide or protein. In one aspect, the composition is frozen, for example flash frozen. In another aspect, the composition is lyophilized or dried in powder form. In a further aspect, it is formulated for administration as a suppository or in ingestible form (e.g., tablet). The composition can further comprise a mixture of the above-noted microspheres, e.g., a mixture containing two or more probiotic bacterium and/or two or prebiofilmics and/or two or more nutritional and/or supplement to support the culturing and/or growth of the probiotic bacterium.

In some embodiments, the prebiotic comprises a water-soluble carbohydrate selected from, but not limited to, one or more of inulin, oligofructose, fructo-oligosaccharide, galacto-oligosaccharide, glucose, maltose, maltodextrins, polydextrose, sucrose, fructose, lactose, isomaltulose, polyols, glycerol, and combinations thereof. In one aspect, the composition further comprises a solid or a liquid carrier, such as a pharmaceutically acceptable carrier.

As is apparent to those of skill in the art, the prebiotic and prebiofilmic are selected in each composition to specifically support the growth of the probiotic bacterium. By way of example only, when the probiotic bacterium comprises *L. reuteri*, the composition comprises an effective amount of sucrose, glycerol and optionally HU polypeptide or protein, to support the growth and maintenance of the probiotic when administered to the subject or patient. Non-limiting examples of prebioflimic compositions include, without limitation, one or more of the polypeptides provided in SEQ ID NOs: 1 to 24, a c-terminal fragment thereof, or a n-terminal fragment thereof, or the additional strains and polypeptides and fragments thereof, such as the full length or the c-terminal fragment or the n-terminal fragment of those provided in Table 4, and equivalents of each thereof. Additional nutritional supplements for the support of other probiotic bacterium are disclosed in Bergey's Manual of Determinative Bacteriology, 9$^{th}$ Ed, Ed. Holt et al., WilliamsWilkins (1994).

Non-limiting examples of a probiotic bacterium for use in the composition includes, without limitation, one or more of *L. acidophilus, L. crispatus, L. gasseri, group L. delbrueckii, L. salivarius, L. casei, L. paracasei, L. plantarum, L. rhamnosus, L. reuteri, L. brevis, L. buchneri, L. fermentum, L. rhamnosus, B. adolescentis, B. angulation, B. bifidum, B. breve, B. catenulatum, B. infantis, B. lactis, B. longum, B. pseudocatenulatum, S. thermophiles*, or a combination thereof. As is apparent to those of skill in the art, one or more bacterium can be combined in a single composition. In some embodiments, the probiotic bacterium is *Lactobacillus reuteri*. The bacteria are available from commercial sources, such as the American Type Culture Collection (ATCC). In one aspect, the one or more probiotic bacterium in the composition supports anti-bacterial immunity. In other aspects, the one or more probiotic bacterium in the composition prevents pathogen colonization and/or limits excessive inflammatory responses by down-regulating cytokine and chemokine production. In some embodiments, the composition further comprises an agent, and the agent is selective against a pathogen, such as a competing pathogen.

The biocompatible microsphere comprises one or more of a biodegradable polymer, a non-biodegradable polymer, a metal, or a combination thereof. In some embodiments, the microsphere comprises a solid core. In some embodiments, the microsphere comprises a hollow core. In some embodiments, the prebiotic is encapsulated within the hollow core of the micro sphere.

In one aspect, the disclosure provides a composition comprising, or alternatively consisting essentially of, or yet further consisting of, a PGLA-biocompatible microsphere, one or more biofilm-generating probiotic bacterium, and a nutritional supplementation comprising one or more of sucrose or glycerol in an amount to support the growth of the probiotic bacterium. The biofilm-generating probiotic bacterium may comprise *Lactobacillus reuteri* ("*L. reuteri*"). The composition may further comprise, or alternatively consist essentially of, or yet further consist of, an effective amount of HU polypeptide or protein. The composition can further comprise a pharmaceutically acceptable carrier or a biocompatible scaffold and is optionally formulated as a suppository.

The size of the microsphere can range from about 0.5 microns to about 100 microns. In certain embodiments, the microsphere is less than about 100 microns in diameter. In other embodiments, the microsphere is less than about 50 microns, or less than about 40 microns, or less than about 30 microns, less than about 20 microns, less than about 10 microns, or less than about 5 microns, or less than 3 microns to 0.5 microns in diameter. In further embodiments, the microsphere is from about 0.5 microns to about 90 microns, or to about 80 microns, or to about 70 microns, or to about 60 microns, or to about 50 microns, or to about 40 microns, or to about 30 microns, or to about 20 microns, or about 10 microns, or about 5 microns, or about 3 microns, or about 2 microns, or about 1 micron, in diameter. Alternatively, the diameter is from about 1 to about 100, or alternatively from about 1 to about 75, or alternatively from about 1 to about 50, or alternatively from about 1 to about 25, or alternatively from about 1 to about 15, or alternatively from about 1 to about 10, microns in diameter.

In some embodiments, the microsphere is a biodegradable polymer, non-limiting examples of such include poly(lactic-co-glycolic acid)("PLGA"); polycaprolactone ("PLC"); chitosan; gelatin; DNA hydrogen; acetalated dextran; poly (lactide); poly(glycolide); poly(lactide-co-glycolide); poly (lactic acid); poly(glycolic acid); poly(lactic acid-coglycolic acid); poly(lactide)/poly(ethylene glycol) copolymers; poly(glycolide)/poly(ethylene glycol) copolymer; poly(lactide-co-glycolide)/poly(ethylene glycol) copolymers; poly(lactic acid)/poly(ethylene glycol) copolymer; poly(glycolic acid)/poly(ethylene glycol) copolymer; poly (lactic acid-co-glycolic acid)/poly(ethylene glycol) copolymer; poly(caprolactone); poly(caprolactone)/poly(ethylene glycol) copolymer; poly(orthoester); poly(phosphazene); poly(hydroxybutyrate); poly(hydroxybutyrate); poly(lactide-co-caprolactone); polycarbonate; polyesteramide; polyanhidride; poly(dioxanone); poly(alkylene alkylate); polyethylene glycol/polyorthoester copolymer; polyurethane; poly(amino acid); polyetherester; polyacetal; polycyanoacrylate; poly(oxyethylene)/poly(oxypropylene) copolymer; and combinations thereof. In some embodiments, the biodegradable polymer is poly(lactic-co-glycolic acid) or PLGA.

In some embodiments, the microsphere comprises a non-biodegradable polymer. Non-limiting examples of non-biodegradable polymers, include without limitation, of one or more of poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly (vinyl imidazole), chorosulphonated polyolefins, polyethylene oxide, and copolymers and blends thereof.

In some embodiments, the microsphere comprises a metal. The metal can be selected from, but not limited to, one or more of cobalt, chromium, gold, nickel, platinum, stainless steel, titanium, tantalum, nickel-titanium, and alloys and combinations thereof.

Pharmaceutical Compositions

The composition can be formulated as a frozen composition, e.g., flash frozen, dried or lyophilized for storage and/or transport. In addition, the composition can administered alone or in combination with a carrier, such as a pharmaceutically acceptable carrier or a biocompatible scaffold. Compositions of the invention may be conventionally administered rectally as a suppository, parenterally, by injection, for example, intravenously, subcutaneously, or intramuscularly. Additional formulations which are suitable for other modes of administration include oral formulations. Oral formulations include such normally employed excipients such as, for example, pharmaceutical grades of mannitol, lactose, starch, magnesium stearate, sodium saccharine, cellulose, magnesium carbonate and the like. These compositions take the form of solutions, suppositories, suspensions, tablets, pills, capsules, sustained release formulations or powders and contain about 10% to about 95% of active ingredient, preferably about 25% to about 70%.

Typically, compositions are administered in a manner compatible with the dosage formulation, and in such amount as will be therapeutically effective for the disease or condition by treated. The quantity to be administered depends on the subject to be treated. Precise amounts of the composition to be administered depend on the judgment of the practitioner. Suitable regimes for initial administration and boosters are also variable, but are typified by an initial administration followed by subsequent administrations.

In many instances, it will be desirable to have multiple administrations of the compositions about, at most about or at least about 3, 4, 5, 6, 7, 8, 9, 10 days or more. The administrations will normally range from 2 day to twelve week intervals, more usually from one to two week intervals. Periodic boosters at intervals of 0.5-5 years, usually two years, may be desirable to maintain the condition of the immune system In some embodiments, additional pharmaceutical compositions are administered to a subject to support or augment the compositions as described herein. Different aspects of the present invention involve administering an effective amount of the composition to a subject. Additionally, such compositions can be administered in combination with modifiers of the immune system. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The carrier may be a solvent or dispersion medium containing, for example, water, ethanol, polyol (for example, glycerol, propylene glycol, and liquid poly(ethylene glycol), and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of undesirable microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

An effective amount of therapeutic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

Processes for Preparing Compositions

This disclosure also provides a method for preparing a composition as described herein, comprising, or alternatively consisting essentially of, or yet further consists of, the steps of admixing, contacting or culturing a biocompatible microsphere with a biofilm-generating probiotic bacterium and a prebiotic. In one aspect, the method further comprises adding or admixing a prebiofilmic that supports the formation and growth of a biofilm by the bacterium. Non-limiting examples of such include, one or more of a DNA binding polypeptide or protein and/or a DNABII polypeptide or protein. The prebiotic utilized in the method comprises a water-soluble carbohydrate, which can be selected from, but not limited to, one or more of inulin, oligofructose, fructo-oligosaccharide, galacto-oligosaccharide, glucose, maltose, maltodextrins, polydextrose, sucrose, fructose, lactose, isomaltulose, polyols, glycerol, and combinations thereof.

Therapeutic Methods

In some embodiments, a method for treating or preventing a disease in a subject is provided, comprising administering to a subject an effective amount of a composition as described above, to a subject in need of such treatment. As used herein, a "subject" intends an animal (e.g., murine, bovine, canine, feline, equine, simian) or a human. Non-limiting diseases to be treated include, but not limited to, psychological disorders, such as depression or anxiety, enteric infectious disease, infection-induced colitis, traveler's diarrhea, inflammatory bowel disease (IBD), colitis, diarrheal illness, vaginosis, wound, burns, psoriasis, dermatitis, tooth decay, periodontitis, sinusitis, or any of chronic and/or recurrent disease that is caused by pathogenic bacteria displacing healthy bacteria or nectrotizing enterocolitis (NEC). In addition, the compositions can be administered to support anti-bacterial immunity, enhancing or supporting the gastrointestinal barrier, or antagonizing disease-related bacterial infection. In some embodiments, the disease is vaginosis. In some embodiments, the disease is colitis or traveler's diarrhea. As is apparent to the skilled artisan, the composition is specifically selected for the disease to be treated. In some embodiments, the composition further comprises a prebiofilmic. In some embodiments, the prebiofilmic comprises a DNA binding polypeptide or protein and/or a DNABII polypeptide or protein, e.g., HU, a fragment thereof and/or an equivalent of each thereof. In some embodiments, the composition is administered as a suppository.

In some embodiments, the composition of the method is administered to provide from about $1\times10^7$ to about $1\times10^9$ CFU/ml of the biofilm-generating probiotic bacterium. In some embodiments, the composition is administered at about 6, 12, 18, 24, 36, 48, and 72 hours. In some embodiments, the composition is administered in a single dose.

In some embodiments, a method of administering a probiotic is provided, comprising administering a dose of a composition as described above, comprising, or alternatively consisting essentially of, or yet consisting of, a biocompatible microsphere, a biofilm-generating probiotic bacterium, a prebiotic, and a prebiofilmic to a subject in need of such treatment. In some embodiments, the composition of the method is administered to provide from about $1\times10^7$ to about $1\times10^9$ CFU/ml of the biofilm-generating probiotic bacterium. In some embodiments, the composition is administered at about 6, 12, 18, 24, 36, 48, and 72 hours. In some embodiments, the composition is administered in a single dose.

Kits

In some embodiments, a kit containing one or more compositions as described herein is provided. The kit comprises, or alternatively consists essentially of, or yet further consists of, a composition as described above, and instructions for use. Alternatively, the kit comprises a microsphere and instructions to make the composition as described above. In one aspect, the bacteria and prebiotic are also provided in the kit.

EXPERIMENTAL EXAMPLES

Example 1

To determine if *L. reuteri* in a biofilm state are superior to planktonic bacteria for establishment in the murine gut, *L. reuteri* was introduced via oral gavage, but instead of repeating the gavage daily, which is typically needed for retention of planktonic bacteria and for beneficial effects 15, 41, a single administration of *L. reuteri* was provided. The *L. reuteri* were grown in biofilm cultures or biofilm grown on poly(lactic-co-glycolic acid) microspheres, such as PLGA, or other FDA approved and biodegradable microspheres (hydrolyzed into lactic acid and glycolic acid) with diameters ranging from 20-300 μm (Beer et al. (1998) Gene Ther. 5:740-746; Kumari et al. (2010) Colloids Surf B Biointerfaces 75:1-18).

Figure 3:
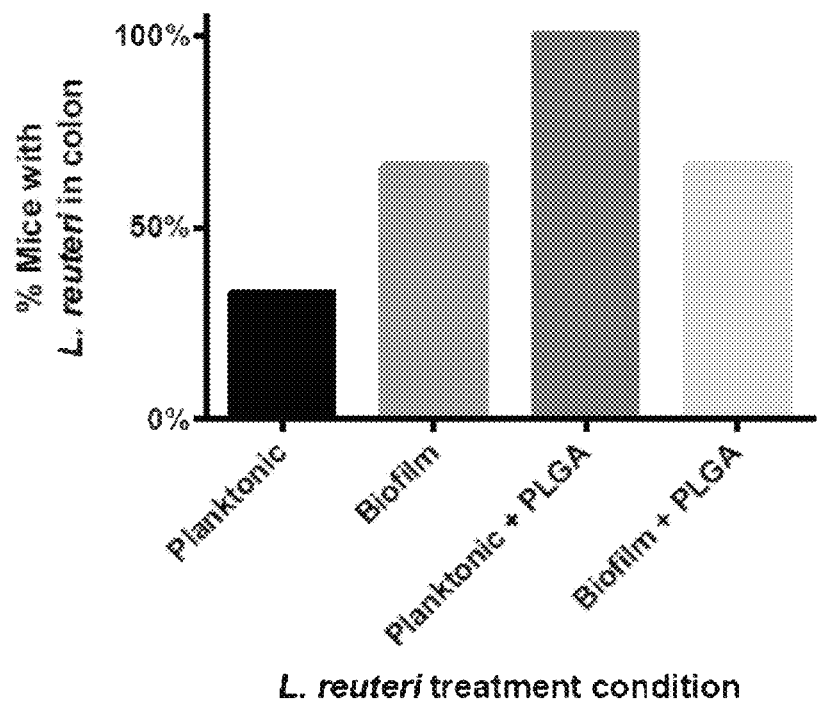
FIG. 3 illustrates that *L. reuteri* in vivo colonization and retention with a single oral administration. Mice (n=3/condition) were administered *L. reuteri* as planktonic, planktonic+PLGA, biofilm, and biofilm+PLGA cultures via oral gavage. After seven days, mice were sacrificed and *L. reuteri* 16S rRNA genes were PCR amplified from the mouse colon. The probiotic was found in a higher percentage of mice that were treated with biofilm cultures or cultures with PLGA present than in planktonic treatments.

Similar preparations of planktonic bacteria were prepared but PLGA microspheres and prebiofilmics were added just prior to gavage. As shown in FIG. 3, the number of mice in which *L. reuteri* was detected in the murine colon after 7 days increased when introduced as a biofilm versus planktonic-grown cells. The presence of PLGA also enhanced the number of mice that were positive for *L. reuteri* compared to conditions where PLGA was not present regardless of whether the bacteria were planktonic or in a biofilm state; this could indicate that *L. reuteri* can initiate attachment to the PLGA, a prelude to biofilm formation, even during this brief interaction (<30 minutes). In the stomach, the only conditions where all mice retained *L. reuteri* was biofilm-grown cells with the addition of PLGA. Thus, it is evident that growing *L. reuteri* in a biofilm in the presence of PLGA enhances colonization and persistence within the stomach and colon compared to planktonic-grown cells.

Example 2

*L. reuteri* vs *C. rodentium* In Vitro

To determine if *L. reuteri* has the capacity to better compete with *C. rodentium* as either a biofilm or in planktonic state in vitro, a competition assay was developed. Here *C. rodentium* biofilms in glass chamber slides (LB medium, 24 hours, 37° C., 5% CO2) were performed. *L. reuteri* (108 colony forming units (CFUs)) was then added as a treatment either as planktonic or in one of three biofilm forms (biofilm, PLGA biofilm, PLGA+HU biofilm; preparation as in FIG. 3) in a medium compatible with both organisms. After 16 hours, the biofilm contents of the chamber slides was removed and aliquots were plated on media selective for *L. reuteri* (MRS) and *C. rodentium* (LB). *C. rodentium* treated with *L. reuteri* biofilm showed a >2 fold decrease in CFU/ml compared to untreated (Table 1), regardless of the state of the introduced *L. reuteri*. More interesting, while all the *L. reuteri* proliferated during the 16 hour challenge, the *L. reuteri* introduced in the form of a biofilm yielded >10-fold more CFUs than when added in planktonic form.

TABLE 1

L. reuteri vs. C. rodentium in vitro competition assays

| Condition[a] | C. rodentium Biofilm (CFU/ml) | L. reuteri Biofilm (CFU/ml) |
|---|---|---|
| C. rodentium biofilm | | |
| Untreated | $1.71 \times 10^9$ | n/a |
| + L. r planktonic | $6.00 \times 10^8$ | $9.00 \times 10^7$ |
| + L. r biofilm | $4.65 \times 10^8$ | $1.12 \times 10^9$ |
| + L. r PLGA biofilm | $5.30 \times 10^8$ | $1.17 \times 10^9$ |
| + L. r PLGA HU biofilm | $4.30 \times 10^8$ | $1.08 \times 10^9$ |
| L. reuteri biofilm | | |
| Untreated | n/a | $2.00 \times 10^9$ |
| + C. r planktonic | $9.20 \times 10^6$ | $1.40 \times 10^9$ |
| + C. r biofilm | $7.90 \times 10^7$ | $2.60 \times 10^9$ |
| PLGA + C. r biofilm | $5.00 \times 10^7$ | $2.50 \times 10^9$ |
| PLGA HU + C. r biofilm | $7.25 \times 10^7$ | $3.45 \times 10^9$ |

[a]Biofilms were treated with $10^8$ CFU of challenge condition

In the converse experiment, the L. reuteri biofilm was introduced first and then treated with C. rodentium ($10^8$ CFUs) in planktonic and biofilm forms. In contrast to the previous experiment, L. reuteri was still able to proliferate increasing in CFUs by >10-fold regardless of the presence of C. rodentium (<2-fold difference between conditions) but C. rodentium did not proliferate during the 16 hour challenge and was actually reduced in CFUs when introduced planktonically. These in vitro results show that C. rodentium biofilms can be effectively challenged with L. reuteri and when introduced in the biofilm state, L. reuteri persist better than planktonic cells. Moreover, preformed L. reuteri biofilms create a poor environment for challenge by planktonic C. rodentium to establish.

Example 3

L. reuteri vs C. rodentium In Vivo

Figure 4:
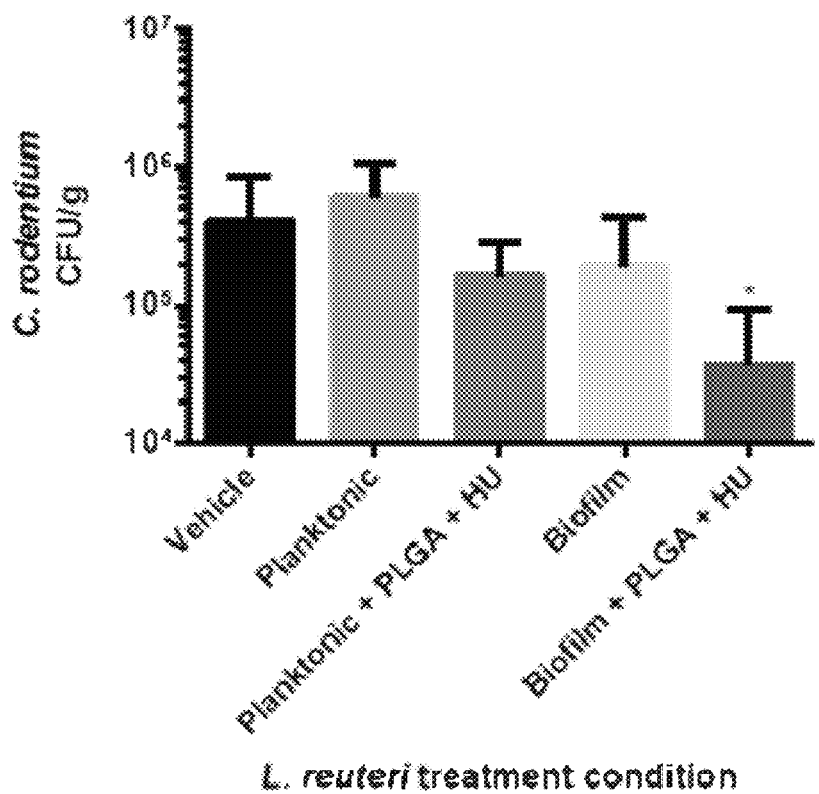
FIG. 4 illustrates that *L. reuteri* biofilm grown with PLGA microspheres and HU reduces *C. rodentium* spleen colonization more effectively than biofilm and planktonic *L. reuteri*. Mice (n=6/condition) were treated with a single oral gavage of *L. reuteri* in one of the following forms: planktonic, planktonic+PLGA+HU, biofilm, and biofilm+PLGA+HU (0.115 μg/ml PLGA, 10 μg/ml HU). After 12 hours the mice were gavaged with *C. rodentium*, and sacrificed 12 days post-infection for necropsy. Only *L. reuteri* biofilm+PLGA+HU showed a statistically significant decrease in *C. rodentium* CFU/g(P=0.0343).

To determine if L. reuteri has the capacity to better compete with C. rodentium as either a biofilm or in planktonic state in vivo, a version of the published competition assay was utilized Mackos et al. (2013) Infect Immun. 81:3253-3263). Briefly, L. reuteri were introduced by oral gavage to mice as described above (L. reuteri planktonic vs biofilm in vivo). After 12 hours, an equal number of planktonic C. rodentium were also added by gavage. After 12 days, all mice were sacrificed for necropsy. Unlike the published work that shows that C. rodentium penetration of brush border epithelia and propagation to the spleen can be thwarted by daily doses of planktonic L. reuteri (Mackos et al. (2013) Infect Immun. 81:3253-3263), there was a statistically significant 10-fold drop in C. rodentium penetration to the spleen in the prebiofilmic treated L. reuteri biofilm with a single dose (FIG. 4). This result is consistent with the magnitude and robustness of prebiofilmic treated probiotic biofilms of having a more durable phenotype in vivo.

Example 4

Characterization of Probiotic Therapeutic Biofilms for Endurance and Robustness

This example has provided strong evidence that the probiotics in the biofilm state provides a superior formulation to bacteria grown planktonically. It also provides one example of how to prepare these biofilms including the frequency of dosing. In addition, the example examines the nature of the biofilm itself to begin to determine why this state out performs planktonic bacteria. Finally, it examines the shelf life of the preparations as a prelude to reduction to practice in human hosts. Combined, this example identifies and characterizes the conditions and constituents for probiotic biofilm preparations.

Example 4.1

Effects of Growth Phase

L. reuteri forms a robust biofilm in vitro and that L. reuteri in a 24-hour biofilm establishes well in the mouse gut were shown. This Example varies the age of the biofilm to determine the optimal age for biofilm establishment.

In vivo L. reuteri biofilms. L. reuteri begins to attach almost immediately when exposed to a surface. After 6 hours sufficient biomass has been produced to be both visible and to start forming the classic biofilm structures (e.g., mushroom, Abee and Kuipers (2011) Curr Opin Biotechnol. 22:133-135). L. reuteri biofilms are isolated at about 6, 12, 18, 24, 36, 48 and 72 hours, that have been grown on PGLA microspheres with HU and calf thymus DNA (as described above) normalizing to CFUs (108) and introducing them by gavage into mice (9 per time point from triplicate experiments). Each mouse is assessed by counting total lactobacilli levels in fecal samples daily for 12 days (cultured on MRS agar).

In addition, this Example uses a real-time PCR method to assess 16S rRNA gene sequence copy numbers for the Lactobacillus genus (including some species of Weisella, Pediococcus, and Leuconostoc due to difficulties with primer specificity) and specifically for L. reuteri. The 16S rRNA gene copy numbers is determined in the feces daily for 12 days, as well as in the colon, cecum, small intestine (including ileum, jejunum, and duodenum), and stomach (including the forestomach) using real-time PCR on Days 1, 3, 6, and 12 post-oral inoculation. Sham mice with and without planktonic cells serve as controls. A significant increase in L. reuteri levels in mice treated with biofilm-grown L. reuteri in comparison to sham or planktonic-treated mice is an indicator of durability and robustness.

Example 4.2

Effects of Growth Conditions

One set of growth conditions has been used to date, standing cultures in MRS media (Jones and Versalovic (2009) BMC Microbiol. 9:35), at 37° C. While not an exhaustive list, here this Example varies the media, the prebiofilmics as well as pH and aerobicity.

Varying growth conditions in vitro. In this Example, other media to grow the biofilms instead of MRS including LB, THYE (THB with yeast extract), mTSB (modified tryptic soy broth) are used as L. reuteri grows in each to varying degrees. In addition, the Example also varies the starting pH to about 5.5, 6, 6.5 or 7 as L. reuteri growth is favored under more acidic conditions. While L. reuteri can be grown microaerophilically under 5% $CO_2$, stressful conditions of times favor biofilm growth (Flemming and Wingender (2010) Nat Rev Microbiol. 8:623-633); here L. reuteri biofilms are also grown in air or in the absence of oxygen (anaerobic chamber). Finally, the Example varies the prebiofilmics of HU (about 0.1, 1, 10, 100 μg/ml) and calf thymus DNA (about 0.1, 1, 10, 100 μg/ml). All the aforementioned biofilms are assessed by CSLM with LIVE/DEAD® staining in triplicate for height, average thickness and biomass as indicators of robust growth.

Varying growth conditions in vivo. Conditions optimal for biofilm growth are compared against both the initial standard conditions as well as the conditions that create the poorest biofilm (control). Biofilms are introduced by oral gavage into 9 mice (from triplicate experiments) for each trial under the conditions optimized in Example 4.1. Sham mice with and without planktonic cells serve as controls. *L. reuteri* levels are assessed as in Example 4.1, on Days 1, 3, 6, and 12 post-challenge.

Example 4.3

Effects of Bacterial Dosing

Dosing of *L. reuteri*; frequency and size. Rhe frequency and or size of dosing improves the durability and robustness of the introduction of *L. reuteri* are determined. *L. reuteri* biofilms are grown on PLGA microspheres with added HU and calf thymus DNA for 24 hours (or an age condition as determined in Example 4.1 and 4.2). *L. reuteri* biofilms are introduced to mice by oral gavage creating a matrix of varying the dose ($10^7$, $10^8$ and $10^9$ CFUs) as well as the frequency (single dose, or daily dose up to 3 days) yielding 9 different conditions. *L. reuteri* levels are assessed in vivo on Days 1, 3, 6, and 12 post gavage as outlined in Example 4.1. Nine mice (from triplicate experiments) for each condition at each time point are used. Sham mice with and without planktonic cells serve as controls.

Example 4.4

Testing Dispersed Biofilm Bacteria

Testing dispersed *L. reuteri* from biofilms. Dispersed bacteria for their endurance and robustness in the mouse gut are examined. *L. reuteri* biofilms can be dispersed by antisera to a DNABII family member (e.g., *E. coli* IHF). Here this Example tests the bacteria released (dispersed) due to anti-IHF treatment. 24 hour *L. reuteri* biofilms (no added PLGA, HU or DNA so as to facilitate dispersal) grown in chamber slides are treated with anti-IHF20. As the peak of dispersal is about 8 to 12 hours after treatment (Goodman et al. (2011) Mucosal Immunol. 4:625-637), conditioned media containing dispersed *L. reuteri* after 12 hours of antibody treatment are used for introduction into mice by oral gavage. *L. reuteri* levels are assessed in vivo on Days 1, 3, 6, and 12 post challenge as outlined in Example 4.1. Nine mice for each time point (from triplicate experiments) with a similar number for controls using planktonic bacteria and optimized biofilm bacteria (Example 4.1 to 4.3) are used.

Biofilms are found to be superior for establishment, persistence and duration of probiotic bacteria in the gut. It is not the biofilm per se that possesses superior features to planktonic bacteria but the bacteria that are dispersed from biofilms. In effect, the biofilm would be acting as a dispersed-bacteria generator. Indeed, physiologic differences in dispersed bacteria as compared to laboratory grown planktonic bacteria (e.g., in antibiotic sensitivity) have been observed.

Example 4.5

Shelf Life

For reduction to practice and ease of use, *L. reuteri* preparations need to be in a sufficiently stable form.

Freezing. *L. reuteri* biofilms have been flash frozen and found no diminution in CFUs and minimum inhibitory concentration or MIC (>2 mg/ml ampicillin; MIC for planktonic *L. reuteri*<4 µg/ml) suggesting *L. reuteri* retains at least one property of its biofilm state, enhanced MIC. Optimized *L. reuteri* biofilms (Example 4.1. to 4.3) for ambient air freezing to −20° C. and −80° C. with and without glycerol (a cryo-protectant; See also Example 2) as well as flash freezing to −80° C. (placing storage tubes with fresh bacterial suspensions in dry ice-ethanol) are examined.

Media are first removed and the resulting biofilm are scraped off and treated to freeze. Bacteria are stored at these temperatures for 1 day, 1 week or 1 month and then thawed at ambient room temperature to be used for introduction into mice by oral gavage. Nine mice from triplicate experiments are used with a similar number for controls using planktonic bacteria and optimized biofilm bacteria (Example 4.1 to 4.3). Each mouse is assessed as in Example 4.1.

Desiccation. Optimized *L. reuteri* biofilms (Example 4.1. to 4.3) via lyophilization after freezing using the optimized technique in Example 4.5 are examined. Desiccated bacteria are stored at room temperature for about 1 day, 1 week or 1 month and then rehydrated with the original biofilm volume of sterile distilled water at ambient room temperature to be used for introduction into mice by gavage. Nine mice from triplicate experiments are used with a similar number for controls using planktonic bacteria and optimized biofilm bacteria (Example 4.1 to 4.3). Each mouse is assessed as in Example 4.1.

Finally, a strain of *L. reuteri* (ATCC23272) is utilized. Additional strains of *L. reuteri* (e.g. strain 100-23, ATCCPTA6475, ATCC55730) are also examined to assess strain differences. As an additional control, *L. reuteri* strains that are commercially available (Fleet® Pedia-Lax™ Probiotic Yums™~100 million CFU/tablet, *L. reuteri* Protectis®DSM 17938 and Gerber® Soothe Colic Drops~100 million CFU/serving (5 drops, ~200 ul), *L. reuteri* Protectis®DSM 17938) are examined. This Example finds that by dissolving each product in water and using them directly in in vitro competition experiments with *C. rodentium* each product is shown to be no better than the strain of *L. reuteri* in planktonic form.

Example 5

Dentification and Characterization of Biodegradable Surfaces and Pre-Biotic Substances to Facilitate the Endurance and Robustness of the Probiotic Biofilms Other types of microspheres as well as inherent cargo that may facilitate either probiotic growth or inhibit pathogens are explored.

Example 5.1

Testing Empty Microspheres

Empty microspheres in vitro, DNA, gelatin, Polylactic acid, Poly-α-caprolactone, chitosan and acetalated dextran are examined in this Example.

While PLGA microspheres are utilized as a surface to grow the biofilms, there are other FDA approved or GRAS biodegradable microspheres that may prove advantageous for the goals. As shown in Table 2, 5 additional types of microspheres are examined (Chellat, F. et al. (2000) J Biomed Mater Res. 51:107-116; Costa, D. et al. (2012)

Colloids Surf B Biointerfaces 92:106-112; Kauffman et al. (2012) ACS Appl Mater Interfaces 4:4149-4155; Kumari et al. (2010) Colloids Surf B Biointerfaces 75:1-18; Sinha et al. (2004) Int J Pharm. 278:1-23; Topuz and O. Okay (2009) Biomacromolecules 10:2652-2661). Thus, DNA can be used as the microsphere material as it is the basis of the EPS for biofilms.

This is an example of an optimization strategy in vitro and in vivo from Example 4. Microspheres from materials in Table 2 and repeat Examples 4.1-4.5 are constructed. Microspheres that fail to support in vitro robust biofilm growth using height, thickness and biomass, as initial metrics; are no longer be considered. Likewise those microsphere types that subsequently fail to surpass in vivo metrics relative to planktonic bacteria are also no longer be considered. Shelf life with and without bacteria, stability at low pH (gastric conditions) are also contemplated.

TABLE 2

Types Of Biodegradable Polymeric Microspheres To Be Tested

| Type of Microsphere | Size Range (μm) | Degradation Products | FDA Approval |
|---|---|---|---|
| PLGA (poly-D,L,-lactide-co-glycolide)[a,b] | 20-300 | Lactic acid, Glycolic acid | X |
| PCL (poly-c-caprolactone)[a,c] | 10-500 | 6-hydroxyhexanoic acid 3-(2-hydroxyethoxy) propanoic acid | X |
| Chitosan[a,d] N-acetyl-D-glucosamine | 20-550 | Glucosamine, | X |
| Gelatin[a] | 35-100 | Amino acids | X |
| DNA (hydrogel)[e,f] | Variable | DNA, ethylene glycol diglycidyl ether | |
| Acetalated dextran[g] | 0.1-10 | Dextran, Acetone, Ethanol | |

[a]Kumari A, 2010, Colloid Surface B, supra.
[b]Beer SJ, 1998, Gene Ther., supra.
[c]Sinha VR, 2004, Int J Pharm., supra.
[d]Chellat F, 2000, J Biomed Mater Res., supra.
[e]Costa D, 2012, Colloid Surface B., supra.
[f]Topuz F, 2009, Biomacromolecules., supra.
[g]Kauffman KJ, 2012, App Mater Interfac., supra.

Example 5.2

Testing Prebiotic Nutrients and Additives that Favor Probiotics as Cargo

The cargo of PLGA is known to diffuse slowly or not even at all relative to the rate of microsphere hydrolysis (Fredenberg et al. (2011) Int J Pharm. 415:34-52). Here microspheres with prebiotic cargo were synthesized and evaluated for their ability to support L. reuteri growth in vitro and in vivo in the mouse models.

This examines nutrients in vitro. As an initial test cargo is loaded into PLGA microsphere during their synthesis (so as to be encapsulated in the interior of the microsphere). These cargos include, but not limited to, inulin, fructo-oligosaccharides, and galacto-oligosaccharides as they support lactobacilli growth. In addition, microspheres with MRS media and/or glycerol are made, as the former is restrictive to Gram-negative bacteria some of which are pathogens and the latter stimulates reuterin production (an antimicrobial molecule believed to give L. reuteri an advantage against competing bacteria). L. reuteri biofilm growth on these microspheres is performed on the conditions observed in Example 4 (or Example 5.1 with a variant microsphere) and is adjudicated by CSLM for height, thickness and biomass.

This example tests prebiofilmics in vitro. As in Example 4.2, the ability of prebiofilmics (HU and DNA) was examined as cargo in PLGA microspheres (and the microsphere types from Example 5.1) to support in vitro biofilm growth. In each case, biofilms are grown under the conditions observed in Example 4 with microspheres synthesized in the presence of HU and or DNA (so as to be encapsulated in the interior of the microsphere) and are adjudicated by CSLM for height, thickness and biomass.

This example tests a combination of prebiotics and prebiofilmics in vitro. Here a matrix of combinations of the two probiotic and two prebiofilmic cargos is created (all 16 combinations of two, all 4 combinations of 3, and the single combination of all 4 equaling 21 total combinations) to find the suitable prebiotics or prebiofilmics. In each case, biofilms are grown under the conditions observed in Example 1 with PLGA microspheres (and the microsphere types from Example 5.1) synthesized in the presence of cargo and are adjudicated by CSLM for height, thickness and biomass.

This example tests optimized components in vivo. Conditions from Example 5.2 that yielded the biofilms are used for in vivo experiments. The four most promising conditions for PLGA microsphere cargo (or the two most promising PLGA and two most promising other type of microsphere from Example 5.1) are tested on nine mice each derived from triplicate experiments. Each mouse is assessed as in Example 4.1 on Days 1, 3, 6, and 12 post-L. reuteri introduction. Sham mice (no bacteria) and planktonic bacteria serve as controls.

Example 5.3

Prebiotic Nutrients that Impede Pathogens

Microspheres containing various probiotic cargos to determine if they support pathogen biofilm growth are examined. The microspheres containing prebiofilmics come into contact with a pathogen (i.e., C. rodentium strain DBS120 (pCRP1::Tn5)) as well as probiotic.

This example tests pathogen impeding nutrients in vitro. The same prebiotic and prebiofilmic substances from Example 5.2, are used as cargo to grow in vitro biofilms. C. rodentium is grown in LB media and used to seed biofilms with PLGA and the aforementioned cargos. Biofilms is adjudicated by CSLM for height, thickness and biomass compared to empty PLGA microspheres.

This example tests pathogen impeding nutrients in vivo. Taking into consideration the results from in vitro biofilm data in Example 5.3, four cargos for C. rodentium biofilm growth and use them in vivo in mouse models are examined. Nine mice for each condition per time point (from triplicate experiments) are used with planktonic C. rodentium and sham (no bacteria) as controls. C. rodentium levels in the stool is determined via culture on all days post oral C. rodentium administration. On Days 1, 6, 12 and 24 post-oral C. rodentium administration, the colon is removed and transected longitudinally so that inflammatory cytokines (e.g., TNF-α), inflammatory mediators (e.g., inducible nitric oxide synthase (iNOS)), and chemokines (e.g., CCL2) can be assessed in half of the colon via real-time RT-PCR. In the second half of the tissue, immunohistochemistry is used to assess leukocyte infiltration into the colon (e.g., F4/80+ macrophages; myeloperoxidase (MPO)+ polymorphonuclear cells). While the aforementioned immune components are necessary for protective immunity against *C. rodentium*, when produced in excess, they can lead to tissue-damaging colitis. Thus, colonic pathology is assessed via H&E staining on the second half of the tissue.

Thus, microsphere biofilm preparations can include alternative types of microspheres and varying cargo. It is Applicants' belief that biofilms (regardless of surface) are superior to planktonic bacteria at seeding probiotic colonization in vivo.

Non-limiting examples cargos, include without limitation specific effectors of innate immunity that reduce inflammation, part of the process leading to dysbiosis. For example, microspheres can comprise conditioned media from *L. reuteri* as *L. reuteri* produce such substances. Likewise other bacteria are within the scope of this disclosure, e.g., *C. rodentium* and *L. reuteri*, in general for pathologies due to dysbiosis.

Example 6

Characterization of *L. reuteri*'s Capacity to Limit or Displace the Murine Gut Enteropathogenic Bacterium *C. rodentium*

Previous examples have identified and characterized the means to create an *L. reuteri* biofilm with the good endurance and robustness in the murine gut while also examining how these conditions might affect the murine enteropathogenic *C. rodentium*. In this Example, the formulations of *L. reuteri* biofilms to determine if they can reduce the effects of *C. rodentium*, or even partially clear introduced or extant pathogen are examined.

Example 6.1

Testing Optimized *L. reuteri* Biofilm Growth Conditions in *C. rodentium* Challenge; Making of *L. reuteri*

In vitro challenge of *L. reuteri* with *C. rodentium*. This Example systematically determines which of the conditions improves *L. reuteri* prophylaxis against *C. rodentium* challenge. As shown in Table 3, the Example systematically performs in vitro experiments where *L. reuteri* is grown in biofilms (about 12, 24, and 48 hours biofilms to reflect varying age) and then treated with varying quantities of planktonic *C. rodentium* ($10^7$, $10^8$ and $10^9$ CFUs). *L. reuteri* biofilm growth conditions from Examples 4.2 (e.g., for prebiofilmics as the media for challenge needs to at least facilitate growth of both bacterial species) as well as 2.1, 2.2 and 2.3 are examined. Mixed biofilms are evaluated after 12 or 24 hours of treatment by CSLM and by plate counts on selective media to determine which species' architecture and numbers dominate under each condition. Controls include each bacterial species without the other under each condition (e.g., the addition of *C. rodentium* added to PLGA microspheres without *L. reuteri* in each chamber slide). All experiments are done in triplicate.

TABLE 3

Systematic Approach To Find Optimal Conditions For *L. Reuteri* Vs. *C. Rodentium* Challenge

| Condition | In vitro | In vivo |
| --- | --- | --- |
| Example 1 | | |
| *L. reuteri* 6, 12, 18, 24, 36, 48, 72 hours biofilm | X | X |
| *L. reuteri* grown in different media (MRS, LB, THYE, mTSB) | X | |
| *L. reuteri* + HU at 0.1, 1, 10, 100 µg/ml | X | |
| *L. reuteri* + DNA at 0.1, 2, 10, 50 µg/ml | X | |
| *L. reuteri* grown at varying pH (5.5, 6, 6.5, 7) | X | |
| Optimal growth conditions | X | X |
| *L. reuteri* dose CFU/ml ($10^7$, $10^8$, $10^9$) | X | X |
| *L. reuteri* dosage frequency (1, 2, 3 days) | X | X |
| Dispersed *L. reuteri* bacteria | X | X |
| Shelf life of *L. reuteri* biofilm preparations (freezing, desiccation) | X | |
| Example 2 | | |
| *L. reuteri* + PLGA, PCL, chitosan, gelatin, DNA, acetalated dextran microspheres | X | |
| *L. reuteri* + nutrient/prebiofilmic/nutrient-prebiofilmic microspheres | X | |
| *L. reuteri* + 4 most promising conditions of loaded microspheres | X | X |
| Prebiotic nutrients that impede pathogens | X | X |
| Example 3 | | |
| *L. reuteri* 12, 24, 48 hours biofilm challenge of *C. rodentium* planktonic $10^7$ $10^8$, $10^9$ CFU | X | X |
| *C. rodentium* challenge of *L. reuteri* at 12, 24, 36 hours post-treatment with *L. reuteri* | | X |
| Established *C. rodentium* infection challenged by *L. reuteri* with top 3 conditions at $10^7$, $10^8$, $10^9$ CFU | X | X |

In vivo challenge of *L. reuteri* with *C. rodentium*. *L. reuteri* biofilm preparations for introduction into animals are prioritized based on the greatest retention or supremacy of *L. reuteri* observed. In addition, *L. reuteri* is prepared based on any successes derived from Examples 4.1, 4.4 and 4.5. In general, *L. reuteri* biofilms are introduced 12 hours prior to oral challenge with *C. rodentium*. Triplicate experiments are conducted for a final sample size of 9 mice for each condition and time point that are assessed at 1, 6, 12, and 24 days post-challenge (peak *C. rodentium* infection occurs at about Day 12). *C. rodentium* levels in the stool are assessed and pathogen-induced colitis is assessed as in Example 5.3. *L. reuteri* levels are also assessed as in Example 4.1. In every case, controls include *C. rodentium* without *L. reuteri* and *C. rodentium* challenge plus planktonic *L. reuteri*.

Example 6.2

Testing Dosing of Challenge Conditions

Dosing frequency and timing of *L. reuteri* with challenge by *C. rodentium* in vivo. This Example tests here how dosing of *L. reuteri* affect its ability to act as a prophylactic against *C. rodentium* challenge. The Example prioritizes the top three *L. reuteri* dosing conditions to reflect the most robust and durable results derived from Example 4.3. The Example then uses these conditions to challenge these *L. reuteri* treated mice with *C. rodentium* (about 12, 24 or 36 hours after the final *L. reuteri* treatment). Nine mice (from triplicate experiments) are used for each condition and time point. Vehicle mice infected with *C. rodentium* and single planktonic *L. reuteri* serve as controls. *C. rodentium* levels and pathogen-induced colitis are assessed on Days 1, 6, 12 and 24 post-challenge as in Example 5.3, with *L. reuteri* levels assessed as in Example 4.1.

Example 6.3

Testing Therapeutic Probiotic Challenge After Pathogenic Treatment Based on the Results in Examples 6.1, and 6.2

In Examples 6.1 and 6.2, conditions for using *L. reuteri* as a prophylactic against the pathologies caused by *C. rodentium* have been optimized. Here *C. rodentium* was introduced before *L. reuteri* to determine what effects challenge with *L. reuteri* has on extant *C. rodentium* pathogenesis.

Challenge of *C. rodentium* by *L. reuteri* biofilms in vitro. This Example shows that *L. reuteri* biofilms effectively challenged *C. rodentium* biofilms more effectively than planktonic *L. reuteri*. Here *L. reuteri* in biofilm form under conditions patterned after the three conditions from Example 6.1 is used. Briefly, *C. rodentium* biofilms (12, 24 or 36 hours) are challenged with *L. reuteri* biofilms ($10^7$, $10^8$ and $10^9$ CFUs). Mixed biofilms are evaluated after 12 or 24 hours after *L. reuteri* challenge of *C. rodentium* biofilms by CSLM and by plate counts on selective media to determine which species' architecture and numbers dominated under each condition, respectively. Controls include each bacterial species without the other under each condition (e.g., the addition of *L. reuteri* to chamber slides without extant *C. rodentium*). All experiments are done in triplicate.

Challenge of *C. rodentium* by *L. reuteri* biofilms in vivo. Here this Example determines if *L. reuteri* biofilms can challenge prior *C. rodentium* infection in the murine model. Three different *C. rodentium* conditions (single gavage 12, 24 or 36 hours) prior to challenge with *L. reuteri* were examined. Four *L. reuteri* biofilm conditions including dosing (Example 6.2) are used to challenge *C. rodentium*. At least two of these conditions are derived from Example 6.1. Nine mice from triplicate experiments are used to test each of these 12 conditions. Pathogen-induced colitis is assessed as in Example 5.3, with *L. reuteri* levels assessed as in Example 4.1.

Here, this Example determines how effective *L. reuteri* introduced in the form of a biofilm is as a prophylactic to *C. rodentium* challenge and as a treatment for extant *C. rodentium* infection. To date, *L. reuteri* under the conditions fails to clear pathogens like *C. rodentium*, so it's particularly important if conditions where a probiotic can prevent or even cure an enteropathogenic infection can be found. Results here provide a rationale for future probiotic approaches.

Finally, the in vitro assays are performed on other pathogens as a prelude to future in vivo experiments. Pathogens included in an in vitro survey are enteric pathogens with different modes of infection, including invasive pathogens (e.g., *Salmonella enterica* subspecies Typhimurium and *Shigella flexneri*), additional A/E pathogens (e.g., Enterohemorrhagic *E. coli* O157:H7; and Enteropathogenic *E. coli*), and toxin-producing pathogens (e.g., *Vibrio cholera* and Enterotoxigenic *E. coli*); the rate limiting step in these experiments is finding co-culturing conditions that sufficiently mimic the in vivo state.

Example 7

Statistical Analyses and Determination of Sample Size

Most of the experiments involve multiple parameters and groups. Thus, two, three, or four factor analysis of variance (ANOVA) are primarily used. As an example of the statistical approach, in Example 4.1, a between subject ANOVA is used with probiotic (i.e., probiotic vs. vehicle control), condition (i.e., biofilm vs. planktonic), and time of culture (i.e., 6, 12, 18, 24, or 36 hours) as between subjects variables. Because different groups of mice are harvested on Days 1, 3, 6, and 12 post-oral inoculation, day of harvest is also used as a between subjects variable.

A significant 4-way interaction is interpreted first using post hoc independent samples t-tests with Modified Bonferroni correction factor applied for multiple comparisons. Afterward, 3-way and 2-way interactions are interpreted via post hoc testing, followed by interpretation of main effects. This general approach is followed for both in vitro and in vivo experiments.

Because of the inherent variability of in vivo experiments, considerable time was spent determining the sample size that would be needed to identify statistically significant differences between groups. A power analysis conducted using preliminary data investigating *C. rodentium* levels after *L. reuteri* administration with six different groups (preliminary sample size of 6), a population mean of 3.95, and population variance of .75, indicated that to obtain statistical significance with $\alpha=0.05$, while maintaining power at 0.8, a sample size of n=9 per condition per time point would be needed. Thus, all animal experiments involve a sample size of nine per treatment and time point. This is accomplished by combining data from triplicate experiments, each containing n=3 mice per treatment and time point.

Probiotics have been widely used for digestive health benefits, although few actually prevent pathogen colonization and reduce the inflammatory response. The effects of probiotic bacteria can be significantly improved by the manner in which they are introduced into the host; specifically by growing them in the form of a biofilm. The data suggest that colonization in vivo by the probiotic *L. reuteri* is greatly enhanced when grown as a biofilm compared to planktonic-grown cells. In addition, when *L. reuteri* was grown in the presence of a biodegradable surface (PLGA), colonization was also increased indicating that the conditions were optimized that allowed a vast improvement in regards to *L. reuteri* establishment within the host.

Unexpectedly and surprisingly, Applicants demonstrated both in vitro and in vivo that treatment of *L. reuteri* as a biofilm in the presence of PLGA prior to challenging with the bacterial pathogen *C. rodentium*, caused a significant reduction in the number of *C. rodentium* compared to planktonic *L. reuteri* treatment. These data reveal that a probiotic can colonize better when presented as a biofilm, indicating that the way in which bacteria are introduced can greatly reflect the outcome of disease.

Example 8

Probiotic microbes have also been shown to reduce anxiety and depression in otherwise healthy humans and laboratory animals. A combination of *Lactobacillus helviticus* and *B. longum* administered daily for 30 days was shown to reduce anxiety and depression in healthy human volunteers and in healthy rats (Messoudi et al. (2011) Br J Nutri. 105:755-764).

This experiment tests whether *L. reuteri* preparations are superior at reducing infectious colitis-induced sickness, anxiety-like, and depressive-like behaviors using the same experimental design as the above-noted studies assessing the effects on infectious colitis itself, with minor modifications.

The primary difference is that animal behavior will be assessed as well as, circulating cytokines, circulating hormones, and neuronal activation in the brain.

To determine whether prophylactic *L. reuteri* can prevent *C. rodentium*-induced sickness, such as anxiety-like and depressive-like behavior, prophylactic treatment with *L. reuteri* biofilms is assessed to determine if *C. rodentium* will prevent bacterium-induced sickness, anxiety-, and depressive-like behaviors. Preparations of *L. reuteri* biofilms that are found to be superior in in vitro assays are administered to mice via oral gavage 12 hours prior to oral challenge with *C. rodentium*. Triplicate experiments are conducted for a final sample size of 9 mice for each condition and time point that are assessed at 1, 6, 12, and 24 days post-challenge (peak *C. rodentium* infection occurs about Day 12). At each time point, animal behavior is assessed for locomotor activity (such as on the open field test), anxiety-like behavior (such as in the light:dark preference test and elevated plus maze), depressive-like behavior (such as on the tail suspension test and Porsolt forced swim task), and sickness behavior (such as with the sucrose preference test). Blood serum cytokines associated with emotional and illness behavior (e.g., IL-1$\alpha$/$\beta$ and IL-6) are assessed on each day. Circulating corticosterone levels will also be assessed. Neuronal activation in the brain, especially the paraventricular nucleus of the hypothalamus, are assessed using c-Fos immunoreactivity.

Whether *L. reuteri* can be used as a therapeutic to treat *C. rodentium*-induced sickness, anxiety-like, and depressive-like behavior also is assessed. For example, the compositions are tested to determine whether treating an established *C. rodentium* infection will reduce sickness, anxiety-, and depressive-like behaviors. Preparations of *L. reuteri* that are found to be superior in in vitro assays are administered to mice via an oral gavage 12, 24, and/or 36 hours after oral challenge with *C. rodentium*. On days 1, 6, 12, and 24 post-*C. rodentium* challenge, animal behavior is assessed for locomotor activity (such as on the open field test), anxiety-like behavior (such as in the light:dark preference test and elevated plus maze), depressive-like behavior (such as on the tails suspension test and Porsolt forced swim task), and sickness behavior (such as with the sucrose preference test). Circulating cytokines associated with emotional and illness behavior (e.g., IL-1$\alpha$/$\beta$ and IL-6) are assessed on each day. Circulating corticosterone levels are also assessed. Neuronal activation in the brain, especially the paraventricular nucleus of the hypothalamus, are assessed using c-Fos immunoreactivity.

These examples permit to modify conditions to create a more robust and long-lasting probiotic, and once established, and allow us to test these conditions in an in vivo model that could ultimately reflect treatments for bacterial infections and human disease.

Example 9

NEC

Probiotic administration may be beneficial in the prevention of NEC. However, probiotics must be administered daily to achieve beneficial effects. Applicants describe herein a novel probiotic delivery system in which the probiotics are grown as a biofilm on the surface of prebiotic-loaded biocompatible microspheres, allowing enhanced and more durable efficacy with only a single treatment.

Following cesarean delivery, neonatal rats were subjected to experimental NEC [hypoxia/hypothermia/hypertonic feeds (stress)]. On day 1, pups were randomized to receive a single enteral dose of the following: (1) vehicle only (100 μL sterile water) (N=32); (2) 1×10$^9$ CFU/mL *Lactobacillus reuteri* (N=9); (3) prebiotic-loaded biocompatible microspheres (N=12); or (4) 1×10$^9$ CFU/mL *L. reuteri* coupled with prebiotic-loaded biocompatible microspheres (N=33). Control pups were unstressed (N=10). Pups were sacrificed when clinical signs of NEC developed or by 96 hours after birth. A verified histologic NEC injury grading system was used to measure the incidence and severity of NEC, with Grade 2 or greater injury considered to be consistent with NEC.

Figure 5:
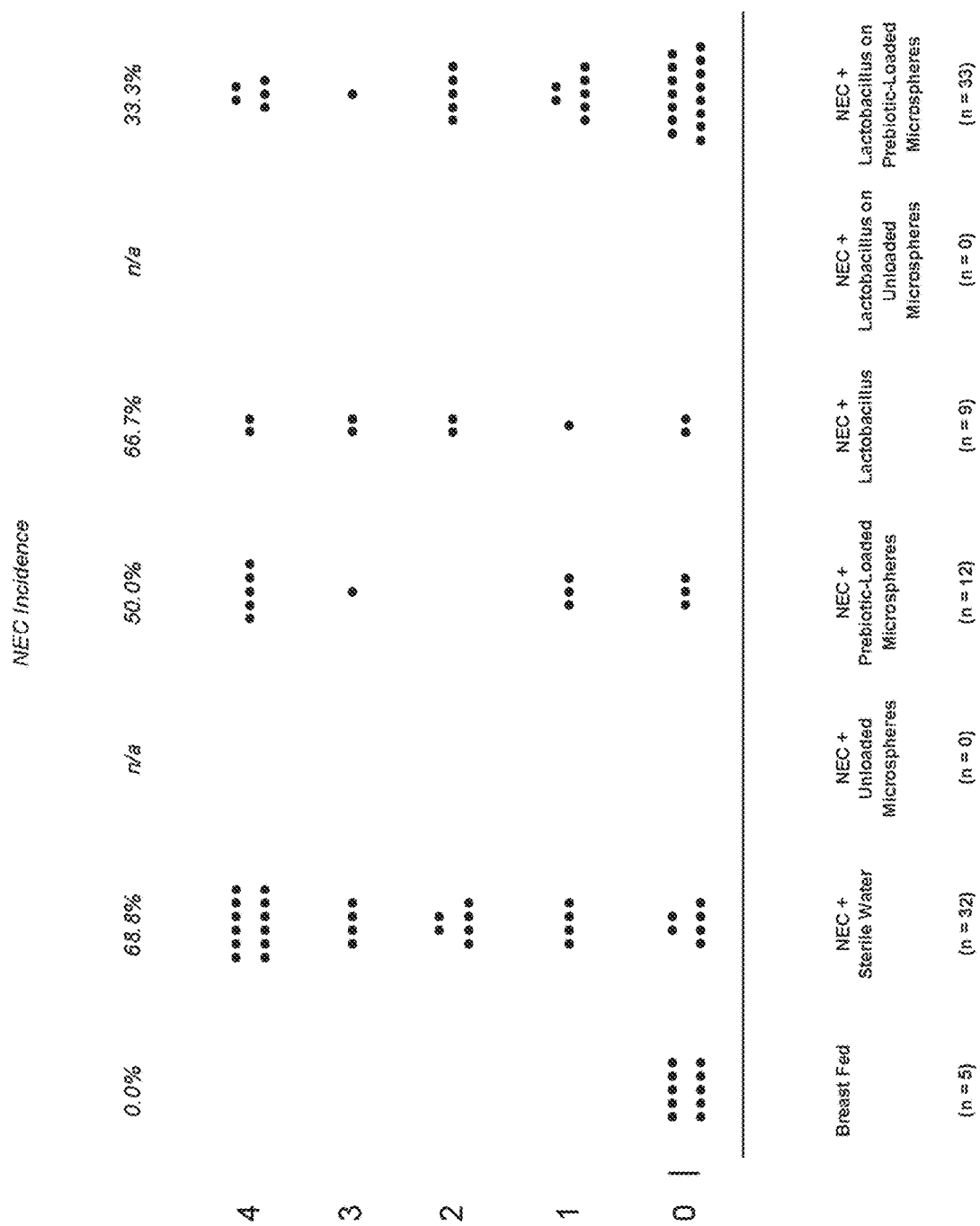
FIG. 5 shows the results of a study establishing that compositions of this disclosure reduce inflammation and antagonize bacterial pathogens in an animal model of NEC.

As graphically depicted in FIG. 5, 69% of untreated stressed pups developed NEC. Compared to untreated stressed pups, 67% of pups treated with *L. reuteri* (p=0.329), 50% of pups treated with prebiotic-loaded microspheres (p=0.364), and 33% of pups treated with *L. reuteri* coupled with prebiotic-loaded microspheres (p=0.003) developed NEC. No unstressed pups developed NEC.

A single dose of a *Lactobacillus* biofilm coupled with prebiotic-loaded biocompatible microspheres reduces the incidence of NEC and therefore is an effective treatment. Without being bound by theory, the compositions as disclosed herein are prophylactic in their use in subjects in need of such treatment.

Example 10

Dessication Tolerance Assay

Another advantage of Applicants' invention is improved long-term survival of probiotic bacteria. A dessication tolerance assay was used to test stability and viability of the bacteria combined with the microspheres. The assay can generally be conducted by performing the following steps. To grow the bacteria culture, transfer 1 ml to a 1.5 ml of the culture to a microcentrifuge tube (1 tube per condition per time period to be tested). Add about 10 μl of hydrated microspheres, trehalose, or nothing to the tube. Incubate the tube for 30 minutes and then pellet the cells via centrifugation. Remove the supernatant and wash the pellet twice with sterile saline. Afterwards, remove all liquid from the pellet. Place the open tube on top of Drierite within an enclosed container and place the container into an incubator at 40° C. After 7 days, remove the tubes, rehydrate, and suspend the pellet in 1 ml of growth medium for 5 minutes. Then, serially dilute and plate for viable colony forming units. Finally, repeat rehydration and plating at 30 days and 90 days.

*P. fluorescens* and a proprietary *Azospirillum* sp. were placed after 90 days incubation at 40° C. while on top of Drierite, a strong desiccant, and then rehydrated and tested for viability. *P. fluorescens* with no microspheres shows a complete loss of colony forming units (CFU) after just one week in these conditions, whereas when incubated with cellulose microspheres, there are 10$^5$ viable cells after 90 days in these conditions. *Azospirillum* sp. shows significant loss of CFUs after 30 days and complete loss after 90 days when grown without the microsphere formulation; however, when stored in harsh conditions with the microspheres, 10$^6$ CFU/ml of *Azospirillum* sp. are viable even after 90 days.

Example 11

Acid Tolerance Protocol (48-Well Plate)

Microspheres filled with *L. reuteri* growth medium as cargo were utilized to provide a surface that leaches buffered nutrients to the bacteria for the formation of a biofilm that enhances survivability at low pH. Bacterial cells with microspheres show over a 2 log increase in viable colony forming units compared to cells without microspheres after sitting in pH 2 gastric acid for 4 hours. Further, L. reuteri with microspheres show increased adherence to mouse colonic cells, addressing the problem of poor colonization and sustainability of orally administered bacteria. Taken together, the novel microsphere formulations not only increase survivability at low pH, but also contribute to colonization of beneficial bacteria in the gut, making L. reuteri a more efficient probiotic.

An acid tolerance protocol assay, such as that used to generate the above information, can generally be conducted by performing the following steps. First, grow 5 ml culture overnight at 37° C. (5% $CO_2$ or anaerobically) and then dilute the culture 1:2500 in a fresh medium. Transfer 500 ml per condition per time period to be tested into a 48-well plate. Transfer ~10 ul of hydrated microspheres or nothing into the well. Afterwards, incubate at 37° C. 5% $CO_2$ (or anaerobically) for 20 hours overnight. At 20 hours, remove the spent media from the biofilm and replace with pH 2 gastric acid. At two and four hours, remove the acid from the biofilm and suspend cells by pipette mixing in the growth medium. Finally, serial dilute and plate the cells.

Example 12

Cellular Adherence Assay

Microspheres filled with L. reuteri growth medium as cargo were utilized to provide a surface that leaches buffered nutrients to the bacteria for the formation of a biofilm that enhances survivability at low pH. Bacterial cells with microspheres show over a 2 log increase in viable colony forming units compared to cells without microspheres after sitting in pH 2 gastric acid for 4 hours. Further, L. reuteri with microspheres show increased adherence to mouse colonic cells, addressing the problem of poor colonization and sustainability of orally administered bacteria. These results show that novel microsphere formulations not only increase survivability at low pH, but also contribute to colonization of beneficial bacteria in the gut, making L. reuteri a more efficient probiotic.

A cellular adherence assay, such as that used to generate the above information, can generally be conducted by performing the following steps. First, grow up a mammalian cell culture line and dilute to ~$10^6$ cells/ml. Transfer 500 ul of the diluted mammalian cell lines to a 48-well plate. Then, grow to confluence (time varies, at least 16 hours) and grow the bacterial culture overnight. Afterwards, transfer 500 ul of the bacterial culture to a 1.5 ml microcentrifuge tube (1 tube per condition per time period). Pellet the bacterial cells via centrifugation and wash the pellet 2-3 times to remove all growth medium. Resuspend the pelleted bacteria in a cell line culture medium. Add either microspheres hydrated in a cell line culture medium, microspheres hydrated in MRS, or nothing to the suspended bacteria.

Remove the growth medium from the confluent mammalian cell culture wells. Aspirate the bacterial conditions with cell line growth medium into mammalian cell culture wells. Incubate at 37° C. 5% $CO_2$. After 1 hour, remove the supernatant spent medium from each well and wash cells with sterile PBS twice to remove non-adhered bacteria. Add 500 ul trypsin to each well to dislodge adhered mammalian cells from the plastic and incubate at 37° C. for 5-10 minutes. Thoroughly mix the liquid in each well to resuspend the mammalian cells. Then, serially dilute and plate to calculate the number of bacteria that remained adhered to the mammalian cells. At 4 and 8 hours, remove the supernatant spent medium from each well and wash cells with sterile PBS twice to remove non-adhered bacteria. Add 500 µl trypsin to each well to dislodge adhered mammalian cells from the plastic and incubate at 37° C. for 5-10 minutes. Thoroughly mix the liquid in each well to resuspend the mammalian cells. Then, serially dilute and plate to calculate the number of bacteria that remained adhered to the mammalian cells.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that the materials, methods, and examples provided here are representative of preferred embodiments, are exemplary, and are not intended as limitations on the scope of the invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

TABLE 4

| Gram (+) - only HU, Gram (−) - all have HU some also IHF | | | |
|---|---|---|---|
| Bacteria strain | Abbreviation | Protein | name(s) |
| S. sobrinus 6715 | Ss | 1310 | (HU) |
| S. pyogenes MGAS10270 | Spyog | Spy1239 | (HU) |

TABLE 4-continued

| Gram (+) - only HU, Gram (−) - all have HU some also IHF | | | |
|---|---|---|---|
| Bacteria strain | Abbreviation | Protein name(s) | |
| *S. gordonii* Challis NCTC7868 | Sg | SGO_0701 | (H1pA) |
| *S. agalactiae* (Group B Strep)2603V/R | GBS | SAG_0505 | (Hup) |
| *S. mutans* UA159 | Sm | Smu_589 | (HU) |
| *S. pneumoniae* R6 | Spneu | spr1020 | (HU) |
| *S. gallolyticus* UCN34 (*S. bovis*) | Sgall | YP_003430069 | (H1pA) |
| *S. aureus* MW2 | Sa | MW1362 | (HU) |
| *S. epidermidis* RP62A | Se | SERP1041 | (Hup) |
| *E. coli* K12-MG1655 | Ec | b1712 | (HimA) |
| | | b0912 | (HimD) |
| | | | (HupA) |
| | | | (HupB) |
| *H. influenza* KW20 Rd | Hi | HI1221 | (HimA) |
| | | HI1313 | (HimD) |
| | | HI0430 | (HupA) |
| *Salmonella enteric serovar typhi* CT18 | Salm | Sty1771 | (HimA) |
| | | Sty0982 | (HimD) |
| *Aggregatibacter actinomycetemcomitans* D11S-1 | Aa | YP_003255965 | (IHFalpha) |
| | | YP_003256209 | (IhfB) |
| | | YP_003255304 | (HU) |
| *P. gingivalis* W83 | Pg | PG_0121 | (Hup-1) |
| | | PG_1258 | (Hup-2) |
| *N. gonorrhoeae* FA1090 (Oklahoma) | Ng | NGO603 | (IHFβ) |
| | | NGO030 | (IHFα) |
| *N. meningitides* MC58 | Nm | NMB_0729 | (HimA) |
| | | NMB_1302 | (HimA) |
| *P. aeruginosa* | Pa | PA3161 | (HimD) |
| | | PA1804 | (HupB) |
| | | PA2758 | (HimA) |
| *H. pylori* 26695 | Hp | Hp0835 | (Hup) |
| *B. burgdorferi* B31 | Bb | BB_0232 | (Hbb) |
| *Moraxella catarrhalis* RH4 | Mc | YP_003626307 | (HimA) |
| | | YP_003627027 | (HimD) |
| | | YP_003626775 | (HupB) |
| *V. cholera* El Tor N16961 | Vc | VC_0273 | (HupA) |
| | | VC_1914 | (HipB) |
| | | VC_1919 | (HupB) |
| | | VC_1222 | (HimA) |
| *Burkholderia cenocepacia* HI2424 | Bc | Bcen2424_1048 | (IHFB) |
| | | Bcen2424_1481 | (IHFA) |
| *Burkholderia pseudomallei* 668 | Bp | BURPS668_2881 | (IHFB) |
| | | BURPS668_1718 | (IHFA) |
| *Mycobacterium tuberculosis* CDC1551 | Mtb | MT_3064 | (HU) |
| *Mycobacterium smegmatis* MC2 | Ms | MSMEG_2389 | (Hup) |
| *Treponema denticola* ATCC 35405 | Td | TDE_1709 | (HU) |
| *Treponema palladium* Nichols | Tp | TP_0251 | (DNA binding protein II) |
| *Prevotella melaninogenica* ATCC 25845 | Pm | PREME0022_2103 | (HupB) |
| | | PREME0022_0268 | (HupA) |
| | | PREME0022_0341 | (Hup) |
| | | PREME0022_0340 | (HimA) |
| *Prevotella intermedia* 17 | Pi | PIN_A0704 | (Hup) |
| | | PIN_A1504 | (Hup-2) |
| | | PIN_0345 | (HimA) |
| | | PIN_0343 | (Hypothetical protein) |
| *Bordetella pertusis* Tohama 1 | Bpert | BP2572 | (IhfA) |
| | | BP3530 | (HupB) |
| | | BP0951 | (IhfB) |
| *Enterococcus faecalis* V583 | Ef | Ef1550 | (hup) |

REFERENCES

T. Abee, and O. P. Kuipers, Understanding Microbial Behavior within and Outside the Host to Improve Food Functionality and Safety, Curr Opin Biotechnol, 22 (2011), 133-5

L. T. Axelsson, et al., Production of a Broad Spectrum Antimicrobial Substance by *Lactobacillus Reuteri*, Microbial Ecology in Health and Disease, 2 (1989)

M. T. Bailey, et al., Stressor Exposure Disrupts Commensal Microbial Populations in the Intestines and Leads to Increased Colonization by *Citrobacter Rodentium*, Infect Immun, 78 (2010), 1509-19

S. J. Beer, et al., Poly (Lactic-Glycolic) Acid Copolymer Encapsulation of Recombinant Adenovirus Reduces Immunogenicity in Vivo, Gene Ther, 5 (1998), 740-6

X. M. Ben, et al., Low Level of Galacto-Oligosaccharide in Infant Formula Stimulates Growth of Intestinal Bifidobacteria and Lactobacilli, World J Gastroenterol, 14 (2008), 6564-8

R. E. Black, et al., W. H. O. Child Health Epidemiology Reference Group of, and Unicef, "Global, Regional, and National Causes of Child Mortality in 2008: A Systematic Analysis", Lancet, 375 (2010), 1969-87

D. Borenshtein, et al., Utility of the *Citrobacter Rodentium* Infection Model in Laboratory Mice, Curr Opin Gastroenterol, 24 (2008), 32-7

C. P. Braegger, and T. T. MacDonald, Immune Mechanisms in Chronic Inflammatory Bowel Disease, Ann Allergy, 72 (1994), 135-41

K. A. Brandstetter, et al., Antibodies Directed against Integration Host Factor Mediate Biofilm Clearance from Nasopore, Laryngoscope (2013)

I. M. Carroll, et al., Alterations in Composition and Diversity of the Intestinal Microbiota in Patients with Diarrhea-Predominant Irritable Bowel Syndrome, Neurogastroenterol Motil, 24 (2012), 521-30, e248

C. Chassard, M. et al., Functional Dysbiosis within the Gut Microbiota of Patients with Constipated-Irritable Bowel Syndrome, Aliment Pharmacol Ther, 35 (2012), 828-38

F. Chellat, M. et al., In Vitro and in Vivo Biocompatibility of Chitosan-Xanthan Polyionic Complex, J Biomed Mater Res, 51 (2000), 107-16

D. Costa, J. et al., Swelling Behavior of a New Biocompatible Plasmid DNA Hydrogel, Colloids Surf B Biointerfaces, 92 (2012), 106-12

J. C. De Man, M.et al., A Medium for the Cultivation of Lactobacilli, J Applied Bacteriology, 23 (1960), 130-35

K. A. Eaton, A. et al., Probiotic *Lactobacillus Reuteri* Ameliorates Disease Due to Enterohemorrhagic *Escherichia Coli* in Germfree Mice, Infect Immun, 79 (2011), 185-91

L. Eckmann, Animal Models of Inflammatory Bowel Disease: Lessons from Enteric Infections, Ann N Y Acad Sci, 1072 (2006), 28-38

H. C. Flemming, and J. Wingender, The Biofilm Matrix, Nat Rev Microbiol, 8 (2010), 623-33

S. Fredenberg, M. et al., The Mechanisms of Drug Release in Poly(Lactic-Co-Glycolic Acid)-Based Drug Delivery Systems—a Review, Int J Pharm, 415 (2011), 34-52

M. O. Freire, P. et al., Development of an Animal Model for *Aggregatibacter Actinomycetemcomitans* Biofilm-Mediated Oral Osteolytic Infection: A Preliminary Study, J Periodontol, 82 (2011), 778-89

S. D. Goodman, K. P. et al., Biofilms Can Be Dispersed by Focusing the Immune System on a Common Family of Bacterial Nucleoid-Associated Proteins, Mucosal Immunol, 4 (2011), 625-37

J. E. Gustave, et al., Targeting Bacterial Integration Host Factor to Disrupt Biofilms Associated with Cystic Fibrosis, J Cyst Fibros, 12 (2013), 384-9

National Institutes of Health, 2013, grants2.nih.gov/grants/guide/pa-files/PA-06-537

P. Hemarajata, and J. Versalovic, Effects of Probiotics on Gut Microbiota: Mechanisms of Intestinal Immunomodulation and Neuromodulation, Therap Adv Gastroenterol, 6 (2013), 39-51

L. M. Higgins, et al., *Citrobacter Rodentium* Infection in Mice Elicits a Mucosal Th1 Cytokine Response and Lesions Similar to Those in Murine Inflammatory Bowel Disease, Infect Immun, 67 (1999), 3031-9

F. Ito, H. et al., Factors Affecting the Loading Efficiency of Water-Soluble Drugs in Plga Microspheres, Colloids Surf B Biointerfaces, 61 (2008), 25-9

S. E. Jones, and J. Versalovic, Probiotic *Lactobacillus Reuteri* Biofilms Produce Antimicrobial and Anti-Inflammatory Factors, BMC Microbiol, 9 (2009), 35

S. S. Justice, B. et al., Aberrant Community Architecture and Attenuated Persistence of Uropathogenic *Escherichia Coli* in the Absence of Individual Ihf Subunits, PLoS One, 7 (2012), e48349

K. J. Kauffman, C. et al., Synthesis and Characterization of Acetalated Dextran Polymer and Microparticles with Ethanol as a Degradation Product, ACS Appl Mater Interfaces, 4 (2012), 4149-55

A. Kumari, et al., Biodegradable Polymeric Nanoparticles Based Drug Delivery Systems, Colloids Surf B Biointerfaces, 75 (2010), 1-18

S. L. Lebeis, et al., Protective and Destructive Innate Immune Responses to Enteropathogenic *Escherichia Coli* and Related a/E Pathogens, Future Microbiol, 3 (2008), 315-28

Y. P. Lin, et al., Probiotic *Lactobacillus Reuteri* Suppress Proinflammatory Cytokines Via C-Jun, Inflamm Bowel Dis, 14 (2008), 1068-83

S. A. Luperchio, and D. B. Schauer, Molecular Pathogenesis of *Citrobacter Rodentium* and Transmissible Murine Colonic Hyperplasia, Microbes Infect, 3 (2001), 333-40

C. Lupp, M. L. Robertson, et al., Host-Mediated Inflammation Disrupts the Intestinal Microbiota and Promotes the Overgrowth of Enterobacteriaceae, Cell Host Microbe, 2 (2007), 119-29

K. Machiels, et al., A Decrease of the Butyrate-Producing Species *Roseburia Hominis* and *Faecalibacterium Prausnitzii* Defines Dysbiosis in Patients with Ulcerative Colitis, Gut (2013)

A. R. Mackos, et al., Probiotic *Lactobacillus Reuteri* Attenuates the Stressor-Enhanced Severity of *Citrobacter Rodentium* Infection, Infect Immun, 81 (2013), 3253-63

X. C. Morgan, et al., Dysfunction of the Intestinal Microbiome in Inflammatory Bowel Disease and Treatment, Genome Biol, 13 (2012), R79

R. Mundy, et al., *Citrobacter Rodentium* of Mice and Man, Cell Microbiol, 7 (2005), 1697-706

J. P. Nataro, and J. B. Kaper, Diarrheagenic *Escherichia Coli*, Clin Microbiol Rev, 11 (1998), 142-201

L. A. Novotny, et al., Structural Stability of *Burkholderia Cenocepacia* Biofilms Is Reliant on Edna Structure and Presence of a Bacterial Nucleic Acid Binding Protein, PLoS One, 8 (2013), e67629

Food and Agriculture Organization of the United Nations and World Health Organization, "Health and Nutritional Properties of Probiotics in Food Including Powdered Milk with Live Bacteria", (2001)

G. A. Preidis, et al., Probiotics Stimulate Enterocyte Migration and Microbial Diversity in the Neonatal Mouse Intestine, FASEB J, 26 (2012), 1960-9

L. A. Sarmiento-Rubiano, et al., Dietary Supplementation with Sorbitol Results in Selective Enrichment of Lactobacilli in Rat Intestine, Res Microbiol, 158 (2007), 694-701

O. Schreiber, et al., *Lactobacillus Reuteri* Prevents Colitis by Reducing P-Selectin-Associated Leukocyte- and Platelet-Endothelial Cell Interactions, Am J Physiol Gastrointest Liver Physiol, 296 (2009), G534-42

V. R. Sinha, et al., Poly-Epsilon-Caprolactone Microspheres and Nanospheres: An Overview, Int J Pharm, 278 (2004), 1-23

N. Takemura, et al., Inulin Prolongs Survival of Intragastrically Administered *Lactobacillus Plantarum* No. 14 in the Gut of Mice Fed a High-Fat Diet, J Nutr, 140 (2010), 1963-9

F. Topuz, and O. Okay, Formation of Hydrogels by Simultaneous Denaturation and Cross-Linking of DNA, Biomacromolecules, 10 (2009), 2652-61

M. Wlodarska, et al., Antibiotic Treatment Alters the Colonic Mucus Layer and Predisposes the Host to Exacerbated *Citrobacter Rodentium*-Induced Colitis, Infect Immun, 79 (2011), 1536-45

Q. Xia, et al., Quantitative Analysis of Intestinal Bacterial Populations from Term Infants Fed Formula Supplemented with Fructo-Oligosaccharides, J Pediatr Gastroenterol Nutr, 55 (2012), 314-20

What is claimed is:

1. A microsphere composition comprising:
a plurality of microspheres, each microsphere comprising dextran cross-linked with epichlorohydrin;
a water-soluble carbohydrate that diffuses from within the microsphere selected from the group consisting of maltose, sucrose, and combinations thereof;
*L. reuteri* strain ATCC 23272, wherein the *L. reuteri* is adhered to the surface of each microsphere; and
a pharmaceutically acceptable carrier.

2. The microsphere composition of claim 1, wherein each microsphere has a diameter of about 1 microns to about 75 microns.

3. The microsphere composition of claim 1, wherein each microsphere has a diameter of about 1 microns to about 100 microns.

4. A single dose composition comprising the microsphere composition of claim 1, wherein the single dose composition comprises between about $1\times10^7$ CFU/ml and $1\times10^9$ CFU/ml of the *L. reuteri*.

5. The microsphere composition of claim 1, comprising between about $1\times10^7$ CFU/ml and $1\times10^9$ CFU/ml of *L. reuteri*.

6. A microsphere composition comprising:
a plurality of microspheres, each microsphere comprising dextran cross-linked with epichlorohydrin, and a water-soluble carbohydrate that diffuses from within the microsphere;
*L. reuteri* adhered to the surface of each microsphere; and
a pharmaceutically acceptable carrier.

7. The microsphere composition of claim 6, wherein the *L. reuteri* is strain ATCC 23272.

8. The microsphere composition of claim 7, wherein the water-soluble carbohydrate is selected from the group consisting of maltose, sucrose, and combinations thereof.

9. The microsphere composition of claim 6, wherein the water-soluble carbohydrate is selected from the group consisting of maltose, sucrose, and combinations thereof.

10. A microsphere composition comprising:
- a plurality of microspheres, each microsphere comprising a biodegradable polymer, and a water-soluble carbohydrate that diffuses from within the microsphere;
- *L. reuteri* strain ATCC 23272 adhered to the surface of each microsphere; and
- a pharmaceutically acceptable carrier.

11. A method for treating necrotizing enterocolitis in an infant in need thereof, comprising administering to the infant in need thereof the composition of claim 1 [a composition comprising:
- about $1 \times 10^7$ and $1 \times 10^9$ CFU/ml of *L. reuteri* plurality of microspheres each comprising: cross-linked dextran and a water-soluble carbohydrate selected from the group consisting of maltose, sucrose, and combinations thereof].

12. The method of claim 11, wherein the [*L. reuteri* is strain ATCC 23272] composition comprises between about $1 \times 10^7$ and $1 \times 10^9$ CFU/ml of *L. reuteri*.

* * * * *

UNITED STATES PATENT AND TRADEMARK OFFICE
CERTIFICATE OF CORRECTION

PATENT NO. : 11,452,748 B2
APPLICATION NO. : 16/449320
DATED : September 27, 2022
INVENTOR(S) : Steven D. Goodman et al.

It is certified that error appears in the above-identified patent and that said Letters Patent is hereby corrected as shown below:

In the Claims

At Column 57, Line 10, In Claim 11 – "[a composition comprising: about $1\times10^7$ and $1\times10^9$ CFU/ml of *L. reuteri* plurality of microspheres each comprising: cross-linked dextran and a water-soluble carbohydrate selected from the group consisting of maltose, sucrose, and combinations thereof]" should be deleted.

At Column 57, Line 17, In Claim 12 – "[*L. reuteri* is strain ATCC 23272]" should be deleted.

Signed and Sealed this
Twenty-fourth Day of January, 2023

Katherine Kelly Vidal
*Director of the United States Patent and Trademark Office*